United States Patent [19]

Kunz

[11] Patent Number: 5,442,169

[45] Date of Patent: Aug. 15, 1995

[54] METHOD AND APPARATUS FOR DETERMINING A MEASURING VARIABLE BY MEANS OF AN INTEGRATED OPTICAL SENSOR MODULE

[75] Inventor: Rino E. Kunz, Steinmaur, Switzerland

[73] Assignee: Paul Scherrer Institut, Villigen, Switzerland

[21] Appl. No.: 958,121

[22] PCT Filed: Apr. 22, 1992

[86] PCT No.: PCT/CH92/00078

§ 371 Date: Jun. 2, 1993

§ 102(e) Date: Jun. 2, 1993

[87] PCT Pub. No.: WO92/19976

PCT Pub. Date: Nov. 12, 1992

[30] Foreign Application Priority Data

Apr. 26, 1991 [CH] Switzerland ............ 1254/91

[51] Int. Cl.[6] .......................................... H01J 5/16
[52] U.S. Cl. .............................. 250/227.21; 250/227.18
[58] Field of Search .................... 250/227.21, 227.14, 250/227.17, 227.18, 227.19, 227.23, 226, 216, 237 G; 385/12

[56] References Cited

U.S. PATENT DOCUMENTS

| | | | |
|---|---|---|---|
| 4,789,213 | 12/1988 | Heywang et al. | 250/227.21 |
| 4,815,843 | 3/1989 | Tiefenthaler et al. | |
| 5,071,248 | 12/1991 | Tiefenthaler et al. | |
| 5,120,131 | 6/1992 | Lukosz. | |
| 5,259,044 | 11/1993 | Isono et al. | 250/227.21 |
| 5,291,014 | 3/1994 | Brede et al. | 250/227.21 |

FOREIGN PATENT DOCUMENTS 3723159  1/1988  Germany.

OTHER PUBLICATIONS

R. E. Kunz, "Gradient Effective Index Waveguide Sensors", Paul Scherrer Institute Zurich, Switzerland, paper submitted to Sensors & Actuators, part B (Elsevier, 1992), Abstract, pp. 1–15, 1 p. references, 1 p. Figure captions, 6 p. drawings.

R. E. Kunz, "Gradient Effective Index Waveguide Sensors" *Sensors and Actuators B*, 11 (1993) pp. 167–176.

R. E. Kunz, "Totally Integrated Optical Measuring Sensors" *Chemical, Biochemical, and Environmental Fiber sensors III*, SPIE vol. 1587 (1991), pp. 98–113.

*Primary Examiner*—David C. Nelms
*Attorney, Agent, or Firm*—Burns, Doane, Swecker & Mathis

[57] ABSTRACT

A method that allows a plurality of variables to be measured with the aid of an integrated optical sensor module. Because all the components necessary for carrying out the method are integrated on the same substrate, the sensor becomes small, compact, stable, malfunction-free and economical. The sensor module substantially comprises a sensor field, an analyzer, and an information field. The method comprises making the variables to be measured interact in sensor fields with guided waves, analyzing the effect on the wave, determining from that the value of the measuring variables, and displaying the results in the information field.

45 Claims, 21 Drawing Sheets

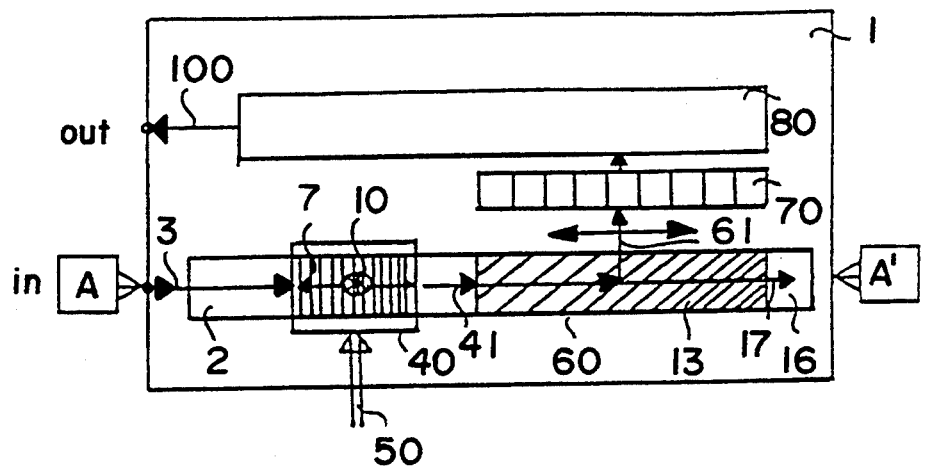
FIG. 10a
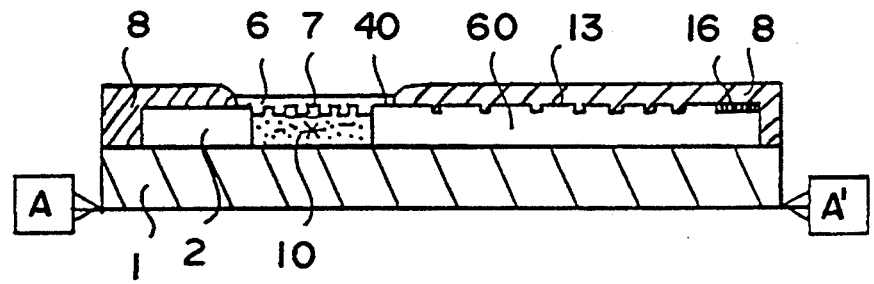
FIG. 10b
FIG. 11a
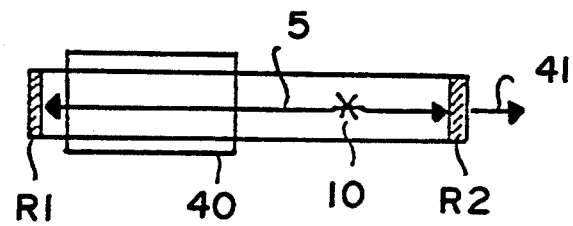
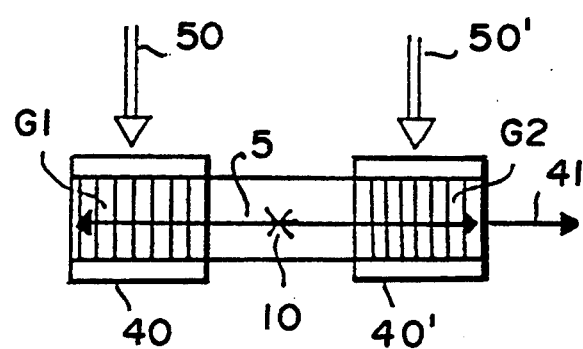
FIG. 11b

METHOD AND APPARATUS FOR DETERMINING A MEASURING VARIABLE BY MEANS OF AN INTEGRATED OPTICAL SENSOR MODULE

FIELD OF THE INVENTION

The present invention relates to a method and an apparatus for determining the value of one or more variables to be measured.

BACKGROUND OF THE INVENTION

An optical sensor for the selective detection of substances and for detecting changes in the refractive index in measurement substances is known from International Patent Application WO 86/07,149. Very high measuring sensitivities can be attained with such an arrangement.

German Patent 3,723,159 discloses a chemical sensor that by means of a selective matrix on a waveguide film induces interactions between the selective matrix and the medium containing the substance and brings about measurable physical changes.

International Patent Application WO 89/07756 discloses an integrated optical interference method for the selective detection of substances and liquid and gaseous samples that achieves high sensitivity with a single film- or strip-type waveguide.

It is a failing of these various arrangements that the waveguide, at best provided with a grating and a sensor layer, is used only as a single component; in other words, the functional sensor comprises a combination of components of the integrated optics (such as waveguides) and discrete optics (such as lasers, lenses, photodetectors, mechanical parts and measuring means). The attendant disadvantages are that it is difficult to adjust, is insufficiently stable, and is highly susceptible to external parasitic induction. Moreover, for many applications, the sensor arrangements take up too much space. Complete systems constructed in this way are also very expensive.

OBJECT AND SUMMARY OF THE INVENTION

An object of the invention is to provide a method and an apparatus for achieving genuinely integrated optical sensor modules in which the aforementioned deficiencies are eliminated.

Exemplary embodiments of the invention are described in detail below, in conjunction with the drawings.

BRIEF DESCRIPTION OF THE DRAWINGS

FIG. 3b is a section along the line A–A' of FIG. 3a;

FIG. 3c is a section along the line B–B' of FIG. 3a;

FIG. 4a shows a sensor module with a uniform Bragg grating on a planar waveguide with a refractive index gradient, in a plan view;

FIG. 4b is a section along the line A–A' of FIG. 4a;

FIG. 4c is a section along the line B–B' of FIG. 4a;

FIG. 5a shows a sensor module with a Bragg grating, with a space frequency varying transversely to the beam 5, on a uniform planar waveguide in a transmission arrangement, in a plan view;

FIG. 5b is a section along the line A–A' of FIG. 5a;

FIG. 5c is a section along the line B–B' of FIG. 5a;

FIG. 9b is a section along the line A–A' of FIG. 9a;

FIG. 10a shows a sensor module with a novel integrated optical light source tunable by the measuring variable;

FIG. 10b is a section along the line A–A' of FIG. 10a;

FIG. 11a is a variant of an integrated optical light source, tunable by the measuring variable, based on a Fabry-Perot resonator;

FIG. 11b is a variant of an integrated optical light source, tunable by the measuring variable, based on a DBR laser with two sensor fields 40 and 40';

FIG. 15b is a section along the line A-A' of FIG. 15a;

FIG. 16b is a section along the line A-A' of FIG. 16a;

FIG. 21a shows a sensor module with amplitude as its module parameter and with an integrated optical spectrometer for determining it;

FIG. 21b is a section along the line A-A' of FIG. 21a, in which an optical cell is used to measure a liquid medium;

FIG. 21c is a section along the line A-A' of FIG. 21a, in which the measuring variable directly influences the optical properties of the waveguide;

FIG. 21d is a section along the line A-A' of FIG. 21a, in which the measuring variable affects the optical properties of a sensor layer applied over the waveguide 2.

FIG. 21e shows a sensor module for the integral measurement of the effect of the measuring variable on the amplitude of the guided wave;

FIG. 23a shows a sensor module with the effective wavelength as its module parameter and with a Fata Morgana arrangement for determining it;

FIG. 23b is a section along the line A-A' of FIG. 23a;

REFERENCES IN THE LITERATURE

Since in the ensuing description of the invention, various individual components of integrated optics that belong to the prior art are used, the corresponding publications will be listed below. In the detailed description, only the abbreviation preceding each will then be referred to. [BARN87]: T. H. Barnes, Appl. Opt. 26/14, 2804–2809 (1987) [BORN80]: M. Born, E. Wolf, "Principles of optics" (Pergamon Press, 6th ed., 1980) [CHEN91]: Y. Chen, A. W. Snyder, Opt. Lett. 16/4, 217–219 (1991) [CREM89]: C. Cremer et al., J. Lightwave Technol., 7/11, 1641–1645 (1989) [DAKI88]: J. Dakin, B. Culshaw (Eds.), "Optical fiber sensors: Principles and components", (Artech House, Boston, 1988) [EBEL89]: K. J. Ebeling, "Integrierte Optoelektronik" [Integrated Optoelectronics], (Springer, Berlin, 1989) [GALE89]: M. T. Gale et al., Tech. Digest Conf. IOOC'89, Kobe, Japan, Vol. 1, 54–55 (1989) [GLAT88]: I. Glatt, O. Kafri, Optics and Lasers in Engineering 8, 277–320 (1988) [HARR67]: N. J. Harrick, "Internal Reflection Spectroscopy", (Wiley, New York, 1967) [HEMM90]: H. Hemme et al., Appl. Opt. 29/18, 2741–2744 (1990) [HUNS84]: G. Hunsperger, "Integrated Optics: Theory and Technology"2nd Edition (Springer, Berlin, 1984) [HUTC87]: L. D. Hutcheseon, "Integrated Optical Circuits and Components", (Dekker, New York, 1987) [KAZO90]: L. G. Kazovsky et al., J. Lightwave Technol. 8/10, 1441–1451 (1990) [KUNZ91]: R. E. Kunz et al., Sensors and Actuators A, Vol. 25, 155–159 (1991) [MINO90]: M. M. Minot, C. C. Lee, J. Lightwave Technol. 8/12, 1856–1865 (1990) [REMI90]: D. Remiens et al., J. Appl. Phys. 68/5, 2450–2453 (1990) [STEV70]: W. H. Stevenson, Appl. Opt. 9/3, 649–652 (1970) [TAKA90]: K. Takada et al., J. Opt. Soc. Amer. A, 7/5, 857–867 (1990) [TAMI79]: T. Tamir (ed.), "Integrated Optics", in Topics in Applied Physics, Vol. 7, 2nd Ed. (Springer, Berlin, 1979) [THOR87]: R. L. Thornton et al., Appl. Phys. Lett. 51/24, 1983–1985 (1987) [URA.90]: S. Ura et al., Appl. Opt. 29/9, 1369–1373 (1990) [VOIR89]: G. Voirin et al., Proc. SPIE, Vol. 1126, 50–56 (1989) [VU..89]: T. Q. Vu, C. S. Tsai, J. Lightwave Technol., 7/10, 1559–1566 (1989) [YIYA89]: A. Yi-Yan et al., IEEE Photonics Techn. Lett. 1/11, 379–380 (1989)

DESCRIPTION OF THE PREFERRED EMBODIMENTS

Figure 1:
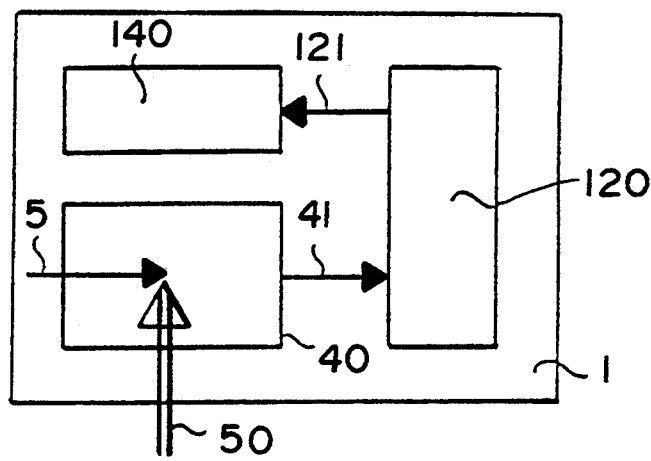
FIG. 1 is a schematic illustration of a sensor module.

FIG. 1 schematically shows a sensor module according to the invention. On a substrate 1, in a manner that for the time being will not be described in further detail, a guided wave 5 in an optical waveguide is excited and delivered to a sensor field 40, by way of which it is made to interact with a measuring variable 50. Once the interaction has occurred, a guided wave 41 is delivered to an analyzer 120, which is located on the same substrate 1, and analyzed. The analyzer furnishes an output variable 121 that is delivered to an information field 140, which for the time being will not be described in further detail, and is kept available there for further use. An essential feature of the invention is that all the components are integrated on the substrate 1.

The energy required to operate the sensor module can be delivered externally to the sensor module or stored in it. Some of the possible ways to do this are electric leads, or light that falls on likewise-integrated photoelectric cells. An especially valuable variant, suitable for chemical or medical purposes, for instance, is the option of obtaining the energy from interaction of also-integrated "active regions" with the surrounding medium. Such active regions may for instance be electrodes, at which electrochemical processes take place from which the sensor module draws the necessary energy. These options may also be combined with one another and with other forms of energy.

The sensor field 40 can be realized in quite various ways. In the simplest case, it is a subzone of the waveguide or of its immediate vicinity that varies its optical properties under the influence of the measuring variable. Some examples and options for varying such subregions will be given in the course of the description of the ensuing drawing figures; some of them can be inferred from German Patent 3723159, International Patent Application WO 86/07149, International Patent Application WO 89/07756, British Patent 2,156,970 and [KUNZ91]. An especially valuable option is to make the properties of the sensor field 40 dependent on the location or time, so as to weight the measurement effect by location or time or to obtain a location- or time-dependent resolution. For instance, the measuring sensitivity may be selected to be high in one subregion of the sensor field, while it is selected to be low in another, or the sensor field may be activated only at certain times, for example with the aid of an integrated clock. The sensor field 40 may be a subregion of either one of the waveguide 2 and the waveguides immediate surroundings, wherein the optical properties of said subregion are influenced by the measuring variable 50, the subregion having at least one of the following properties: magnetooptical, electrooptical, nonlinear optical, piezooptical, thermooptical, chemooptical, elastooptical, biooptical acoustooptical, and optical properties dependent on one or both the type and intensity of incident particle radiation.

The analyzer 120 may comprise various components, such as optical and electronic components. Exemplary embodiments will be given below; preferably a first optical stage, a photodetector, and an electronic stage will be used. In general, however, the analyzer may be considerably more complicated in design and may for instance also include other, particularly non-optical, sensor elements, and may jointly use the signals of those elements in producing the output signal 121. For complex or high-precision applications, the analyzer may also have artificial intelligence and may generate closed-loop control signals, for instance. Examples are to include the temperature in order to compensate for temperature-dependent drift phenomena, and to derive complex signals from the interaction of more than one measuring variable in various sensor fields. A sensor module of this kind can for instance be used as an "artificial nose" for gas analysis.

The information field 140 may be embodied either simply, for instance in the form of an electrical terminal, or quite complexly. Examples are thermocouplers for temperature regulation, antennas for broadcasting electromagnetic waves, light sources of variable frequency for monitoring photochemical processes in the sphere of influence of the information field, and electrodes or biologically active materials for inducing signals in the nerves of the human body as a function of the measuring variables. Because of the complete integration according to the invention, sensitive "autonomous" sensors can be achieved, examples being an artificial nose for a patient who has lost his sense of smell from disease or an accident, and in that case the complex signal represents an odor.

Figure 2:
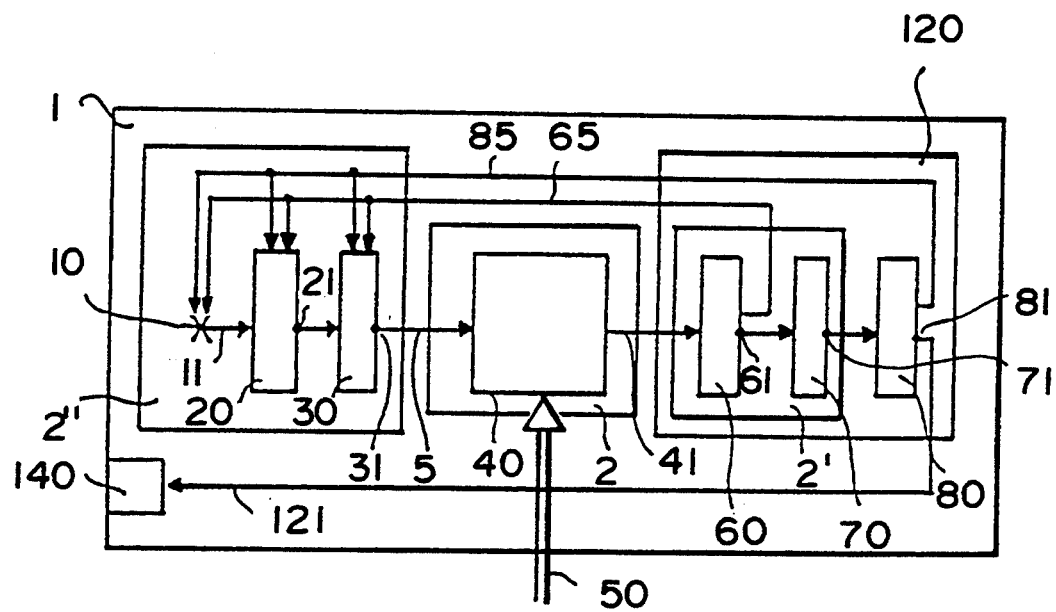
FIG. 2 is a more-detailed schematic illustration of a sensor module.

FIG. 2 schematically shows an exemplary embodiment of the invention. Film or strip waveguides 2, 2' and 2'' and a light source 10 are located on the substrate 1. The radiation 11 produced is converted into a parallel beam via a light forming stage 20 and is delivered as a guided wave 21 to an optical filter 30 and then to the sensor field 40, where it is in interaction with the measuring variable 50. The guided wave 41 emerging from the sensor field 40 is delivered to an optical analyzer 60, whose optical output signal 61 is converted in a detector 70 into an electrical signal 71 and carried to the electrical signal processing unit 80. The signal processing unit 80 generates an output signal 81 and selectively generates a feedback signal 85 for closed-loop control. The output signal 81 is delivered via the output line 121 to the information field 140, from which it is removed from the sensor module, while the feedback signal 85 is returned for closed-loop control purposes to the light source 10 and/or the light forming stage 20 and/or the optical filter 30. For closed-loop control purposes, an optical signal 65 may likewise be sent back to the light source 10 and/or the light forming stage 20 and/or the optical filter 30. The analyzer 120 here comprises the components 60, 70 and 80.

For producing the waveguides, various methods known in integrated optics and thin-film technology may be employed, such as various sputtering and deposition processes, ion exchange, and deep drawing. Depending on the method, various waveguide types, such as stepped or gradient waveguides, are also possible. The waveguides are often shown as single-layer waveguides in the drawings. Naturally, multiple-layer waveguides may also be used, and additional layers (called buffer layers) may be necessary, for instance between the substrate and the waveguide.

In a preferred arrangement, the light source 10 is produced directly in the waveguide [THOR87], but arrangements may also be selected in which the light source 10 is mounted in an additional layer above, below or next too the (passive) waveguide, and the light is coupled into the waveguide, for instance with the aid of the transverse-damped wave, via gratings [CHEN91] or by so-called butt-coupling [REMI90]. In a sensor module with an optical input, the wave 5 may also be excited via an optical fiber. These coupling methods are prior art. The light source 10 is preferably a laser or a narrow-band light emitting diode (LED). A broader-band light source may also be used, however, in which case a suitable spectrum is filtered out with the aid of an optical filter 30, see FIG. 2); for instance, see [CREM89] and [KAZO90]. It will be understood that the filter 30 may be dispensed with if the light source itself already has a suitable spectrum.

Depending on the waveguide type, the light forming stage 20 (see [MINO90] and [VU..89]), serves either to reshape the light emitted by the light source into one or more guided waves of a planar waveguide, or to couple the light into one or more strip waveguides (beam forming). The wave parameters, such as the beam width and curvature of the wave fronts, can be fixed in a suitable manner. It will be understood that the light forming stage may be dispensed with if the light source already emits a suitable beam of light or can for instance be coupled directly to a strip waveguide.

Figure 3C:
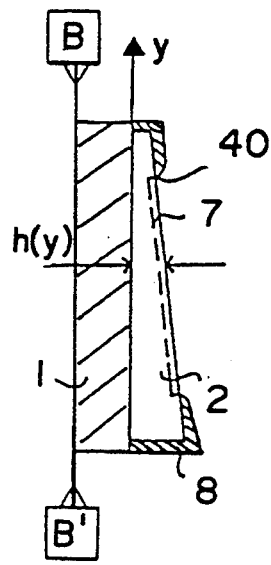
Figure 3A:
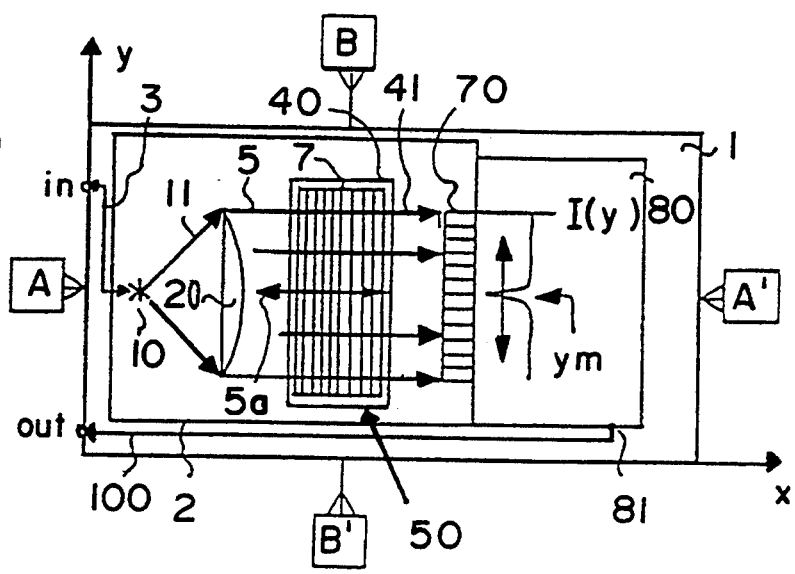
FIG. 3a shows a sensor module with a uniform Bragg grating on a planar waveguide with a thickness gradient, in a plan view.
Figure 3B:
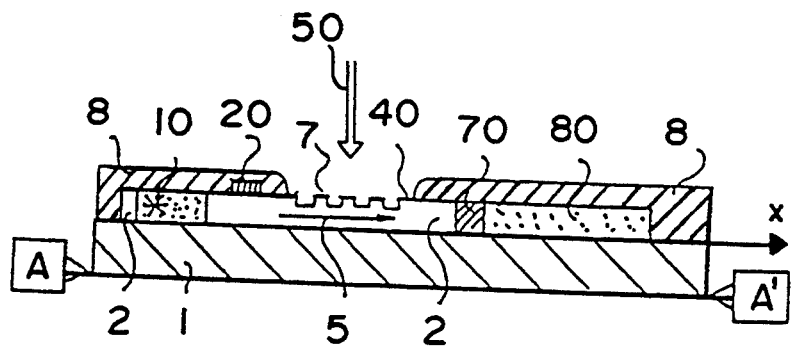

FIGS. 3a through c schematically show an exemplary embodiment of the invention. A waveguide 2, in which a light source 10, for instance a laser diode, that is operated via an input line 3 is disposed, is located on the substrate 1. The radiation 11 produced is carried to an integrated collimator optical element 20, where it is converted into a parallel beam 5. Various techniques may be employed for making the collimator optics, such as using one or more geodesic, Lümeburg, Fresnel, grating, or other lenses [HUNS84, 279-80; MINO90; VU..89]. In the form of a guided wave, the beam strikes a sensor field 40, in which a defraction grating 7 has been produced by a known method in the waveguide itself or in the vicinity of the waveguide boundary faces. Such gratings are known to have very sharply defined resonances with respect to transmission and reflection of guided waves (for instance, see [HUTC87, 34-54; TAMI79, 73-78]).

The measuring variable 50 is in interaction with the guided wave in the region of the sensor field 40, somewhat as described in International Patent Application WO 86/07149, German Patent 3723159, International Application WO 89/07756 or British Patent 2,156,970. In contrast to those patent references, however, at least in the region of the grating 7, the waveguide 2 has a thickness gradient h(y) in the y direction, which produces a corresponding gradient with the effective refractive index N(y). The concept of the effective refractive index and its dependency on the thickness of the waveguide has been described, for example in [TAMI79, 13-81].

In the ensuing description here, it will initially be assumed that the light source emits monochromatically and at a constant frequency v. In that case, the effect of the gradient N(y) is that the above-described resonance condition of the Bragg grating becomes location-dependent and is met only at one specific position $Y_m$. Meeting the resonance condition means here that of the incident beam at position $y_m$, a partial beam 5a is reflected, while the incident wave 5 is transmitted practically completely at the other points. The position $y_m$ depends in particular on the parameters of the waveguide and of the grating, on the frequency v and on the course N(y). The method of this exemplary embodiment of the invention is based on a variation N(y)+dN of the course N(y) based on the interaction of the varying measuring variable 50 with the guided wave at the location of the grating 7. In accordance with the above discussion, this variation dN effects a displacement of the location $y_m+dy_m$ where the resonance condition is met; that is, there is a resultant lateral beam shift $dy_m$ of the portion 5a of the beam 5 reflected at the grating. Because of the relationship $dy_m=dy_m(dN)$ of the beam shift $dy_m$ and because of the variation dN, primarily effected by the measuring variable 50, the value of the measuring variable 50 can now be determined via the displacement $dy_m$. In other words, the method is based on the fact that the value of the measuring variable 50 affects the module parameter (in this case, the location $y_m$ of the Bragg grating resonance) in such a way that the value of the measuring variable can be determined from the value of the module parameter.

The location $y_m$, or the magnitude of the displacement $dy_m$, can be measured in various ways. In the example of FIG. 3, the transmitted beam 41, modified by the interaction, is carried at the intensity distribution I(y) to the detector 70, which is suitably embodied as an array or as a position-sensitive detector. An electrical signal $U(y_m)$ dependent on the location $y_m$ is now available at the output of this detector for further processing in the electrical unit 80. The processed signal 81 can be picked up at the sensor module via the line 100.

Outside the sensor field 40, the top of the sensor module is provided with at least one protective layer 8, which serves the purpose of passivation and is preferably of plastic (such as polymer), or is produced by some other process of thin-film technology.

Figures 4A, 4C:
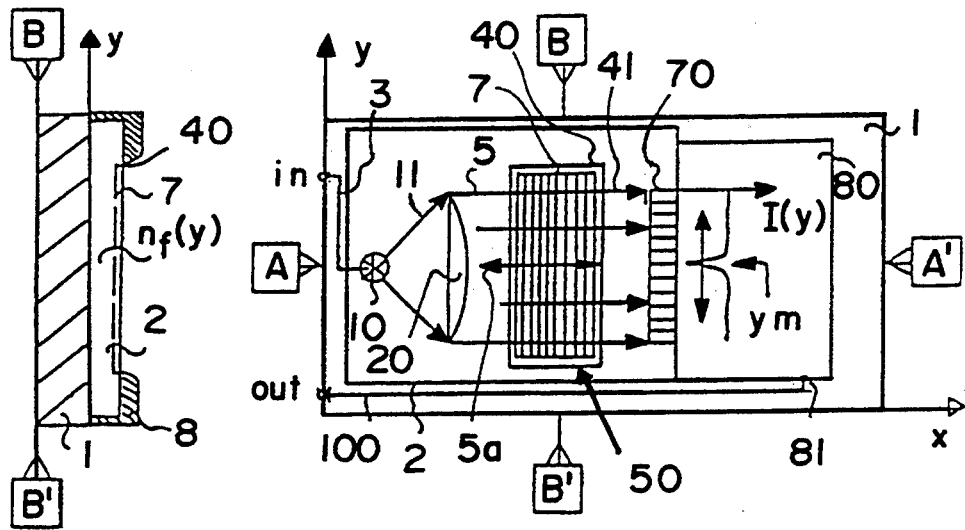
Figure 4B:
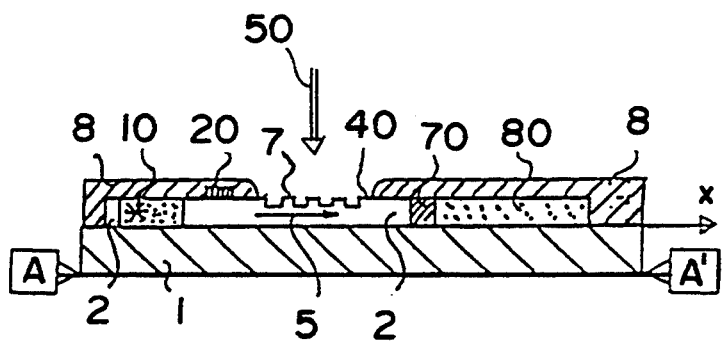

FIG. 4 shows another exemplary embodiment. The difference from FIG. 3 here is the design of the waveguide 2, which at least in the grating region 7 of the sensor field 40 has a refractive index gradient $n_f(y)$, which results in an N(y) gradient. The remainder of the description of FIG. 2 applies logically here as well. In particular, this method is likewise based on a variation N(y)+dN of the course N(y), because of the interaction of the varying measuring variable 50 with the guided wave 5 at the location of the grating 7. The value of the measuring variable 50 is also determined here with the aid of the relationship $dy_m=dy_m(dN)$ between the beam shift dy, and the variation dN primarily effected by the measuring variable 50. In other words, in this example as well, the module parameter is the location $y_m$ of the Bragg grating resonance, which is determined by the value of the measuring variable.

Figures 5A, 5C:
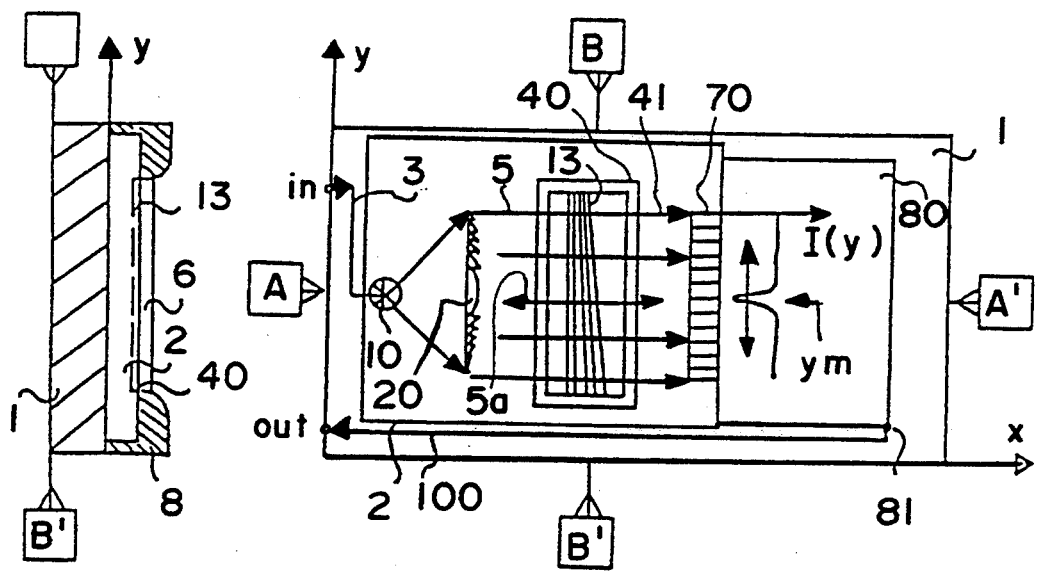
Figure 5B:
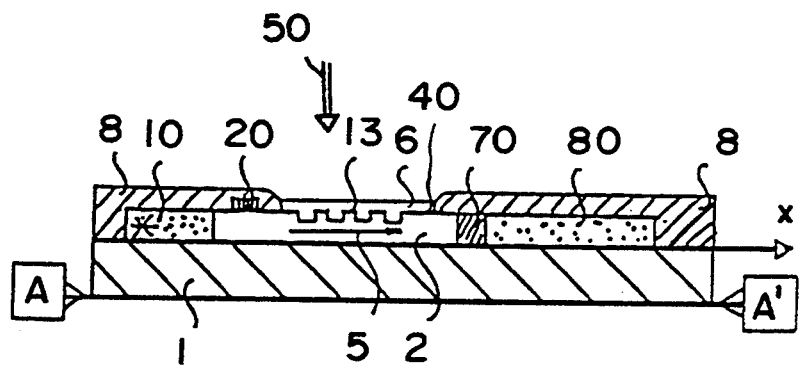

FIGS. 5a through c show a further exemplary embodiment. The difference from FIGS. 3 and 4 here is the design of both the waveguide and the grating region. The waveguide is planar and uniform; that is, it has a refractive index profile that is independent of x and y, as is usual in modern integrated optics [EBEL89, 49-62]. As a special feature, however, a nonuniform grating 13 with a locally variable space frequency K(y) is used here (this is known as a "chirped grating"). For a definition of the space frequency $K=2\pi/\lambda$ in gratings with a constant period lambda, see for example [EBEL89, 62-68]. Gratings with a variable space frequency have been described in U.S. Pat. Nos. 3,814,498 and 4,776,661, for example. In contrast to these patents, the periodicity of the grating involved in the present case varies transversely to the beam direction, and the wave striking the grating 13 is quasimonochromatic. Another option is to use gratings whose depth or profile varies over the grating region. In all cases, either a continuous variation or an erratic variation, in other words the use of "multiple gratings" is possible The purpose of the nonuniform grating 13 is to create a location-dependent resonance condition. Since because of the uniform waveguide the effective refractive index N is at least approximately constant, the resonance condition here is determined substantially by the frequency of the light source 10, by N and by the space frequency K(y). If the measuring variable 50 now varies, than the effective refractive index varies by dN, which in this example as well results in a beam shift $dy_m$. The reflected partial beam 5a and the transmitted beam 41 having an intensity distribution I(y) and the resonance location $y_m$ dependent on the measuring variable 50, are analogous to FIGS. 3 and 4. The description of FIGS. 2 and 3 again applies as appropriate. Once again, the module parameter is the location $y_m$. FIGS. 5b-c show a sensor layer 6 which is applied over the grating region 13 in the sensor field 40 and mediates the interaction of the measuring variable 50 with the wave 5. This sensor layer 6 may also be more complicated in structure, or it may be absent, or it may be realized in the waveguide itself (see description of FIGS. 1 and 21b-d).

Figure 6A:
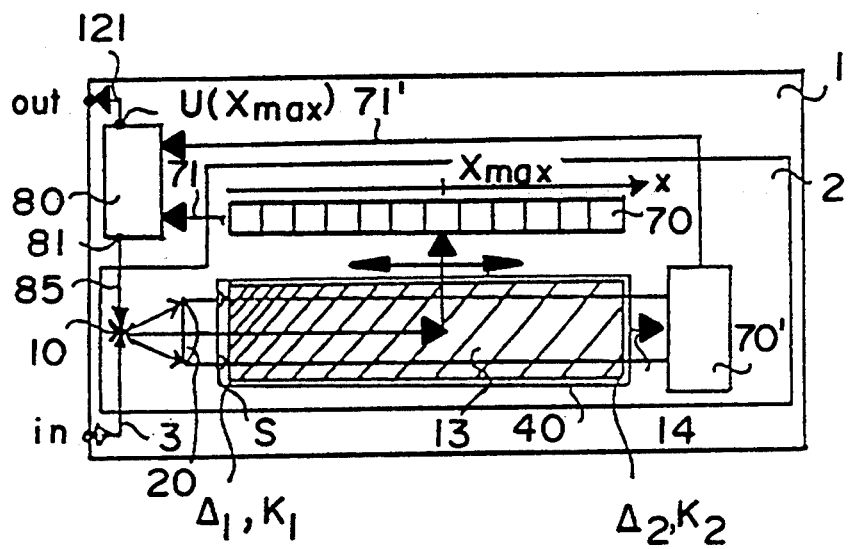
FIG. 6a shows a sensor module with a Bragg grating, with a space frequency varying longitudinally to the beam 5, on a uniform planar waveguide in a reflection and transmission arrangement, in a plan view.

FIG. 6a shows a further exemplary embodiment. The substrate 1, the planar waveguide 2, the electric lead 3, the light source 10, the collimator optics 20 and the light beam 5 are as described for FIG. 3. The waveguide 2 is now provided in the grating region with a chirped grating 13, whose periodicity lambda (x) in the beam direction increases continuously from a value lambda 1 up to a value of lambda 2. The effect of such a grating in a passive version, in other words without a sensor field, is described in U.S. Pat. No. 3,814,498. There, space is made for a sensor field 40 above the chirped grating 13, and the measuring variable 50 interacts with the guided wave 5 traveling in the waveguide by way of this sensor field 40. To simplify the discussion, it will now be assumed that the light source 10 is intended to shine monochromatically, and that a uniform waveguide is used. Then the beam 5 will penetrate the sensor field 40 far enough so that the resonance condition, in other words the maximum Bragg reflection, is met at a point marked $x_{max}$. There the great majority of the incident radiation is reflected and carried as an optical signal directly to the detector 70. The module parameter, in this case the location $x_{max}$, is determined by the value of the measuring variable 50, in a similar manner to that of FIGS. 3 through 5; that is, the variation in the measuring variable 50 effects a variation dN of the effective refractive index N and hence a displacement of the resonance location to a location $x_{max}+dx_{max}$. The guided wave 5 in the grating region 13 in a sense selects the point that has the appropriate space frequency $K=2/\text{lambda}$.

For high-precision applications, the unreflected portion 14 can be carried to a second detector 70' and be used, via a correction signal 71', for monitoring or correcting the electrical evaluation, for instance in order to correct interfering factors resulting from fluctuations in the light source. A further option is to effectively correct such fluctuations with the aid of a closed-loop control signal 81 via a line 85 to the light source 10. The further steps for producing the output signal $U(x_{max})$ are similar to those of FIGS. 3 through 5.

The dynamic range of the sensor is defined by the space frequency range $K_1 \ldots K(x) \ldots K_2$. If the dynamic range is small, then $K_1 < K_2$ or $K_1 > K_2$ may be selected, while for wide dynamic ranges $K_1 > K_2$ (as shown in FIG. 6a) is advantageous, in order to avoid miscellaneous interference that could be caused by orders of diffraction as they propagate. The resolution depends on the variation rate dK/dx. To achieve high resolution, a slow variation of K(x) is necessary. One option of interest is to select the local course K(x) as nonlinearly continuous or noncontinuous, such that both a wide dynamic range and, within a selected subrange, a high resolution are obtained.

Figure 6B:
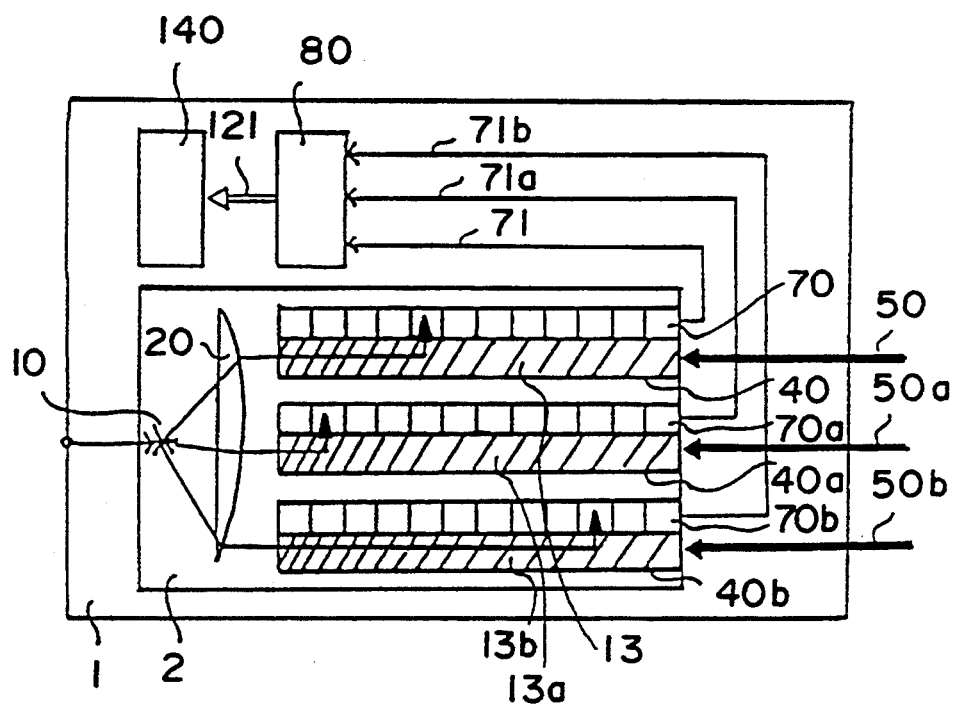
FIG. 6b shows a sensor module with a Bragg grating, with a space frequency varying longitudinally to the beam 5, on a uniform planar waveguide in a reflection arrangement, in a plan view.

Another option is to couple a plurality of integrated optical gauges together with detectors to the same light source and thus to be able to detect various measuring ranges and/or measuring variables simultaneously (integrated optical sensor array). A corresponding exemplary embodiment is schematically shown in FIG. 6b. In this example, because there are three measuring channels with sensor fields 40, 40a, 40b, detectors 70, 70a, 70b and signals 71, 71a, 71b, three measuring variables 50, 50a, 50b can be measured simultaneously. In the information field 140, via the signal processing unit 80, output signals 121 for the various measuring channels, or one complex signal, can be generated, depending on the intended use. It will be appreciated that depending on the embodiment of the sensor fields, either three different measuring variables (for instance one chemical, one optical and one magnetic variable) or only one measuring variable but at three different points can be detected. This application is of interest, for instance for making an artificial nose, in which the complex signal 121 represents a certain odor.

Figure 7A:
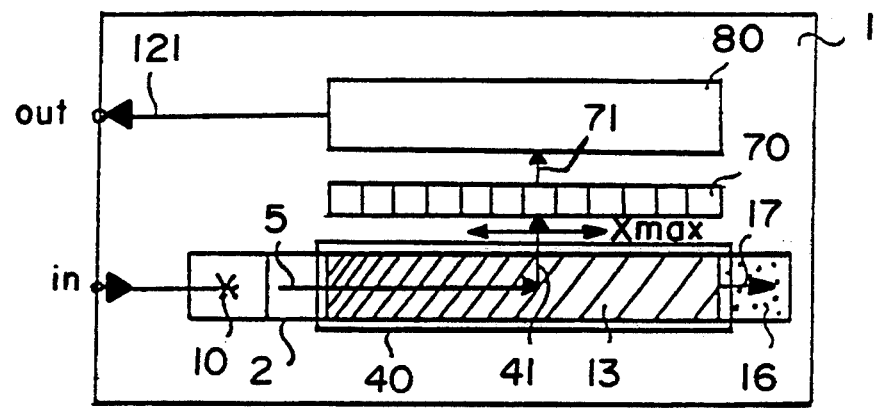
FIG. 7a shows a sensor module with a Bragg grating, with a space frequency varying longitudinally to the beam 5, on a strip waveguide in a reflection arrangement, in a plan view.

FIG. 7a shows a further exemplary embodiment. The light source here is a laser 10, which is coupled directly to a passive strip waveguide 2 (see [THOR87], for example). The sensor field 40 is located here directly above the strip waveguide 2 in the region of the nonuniform Bragg grating 13. An absorber 16 prevents the transmitted light 17 from striking the detector 70 as interfering light, so the detector signal 71 depends only on the position $x_{max}$ of the reflected proportion 41 of the light. This sensor module represents a fully optoelectronically integrated version, with electrical connections.

Figure 7B:
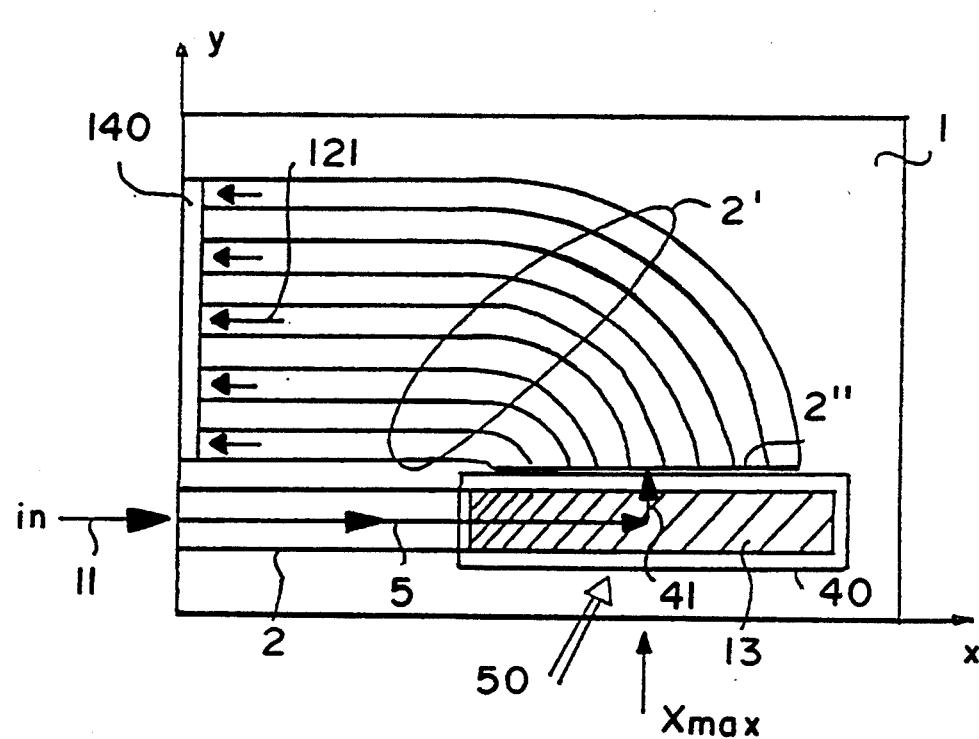
FIG. 7b shows a sensor module with a Bragg grating, with a space frequency varying longitudinally to the beam 5, on a strip waveguide, and with a strip waveguide array.

FIG. 7b shows an example for fully optical integration with purely optical connections, such as fibers. The entry into the sensory module 1 is made via an optical fiber 11, which is coupled to the strip waveguide 2. Once again, the module parameter is the location $x_{max}$. The end face 2" of the strip waveguide array 2' acts as an analyzer. The information field 140 may be directly the exit face of the array 2' in which case the readout is done by the naked eye. The output signal here is the number of the strip waveguide in which the highest light power is observed. As a further option, via the center strip waveguides 2', the purely optical outputs 121 of the sensor module are made available in the information field 140, so that they can be carried away via a fiber-optical cable.

Figure 8A:
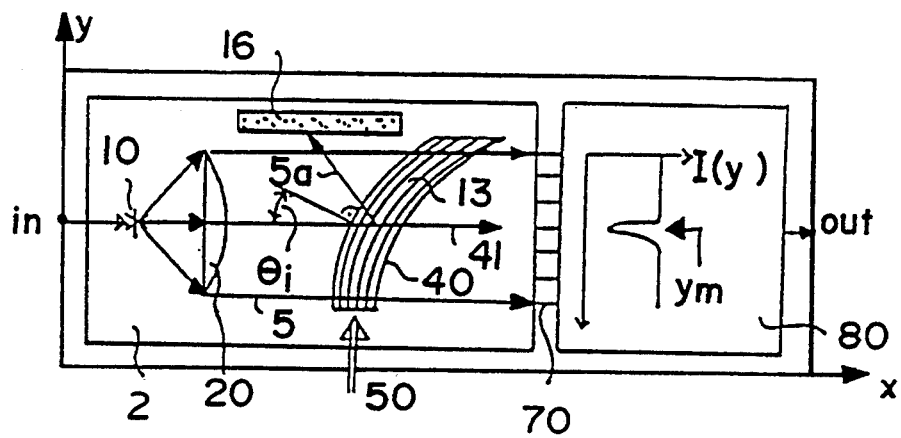
FIG. 8a shows a sensor module with a nonuniform Bragg grating and an angle-dependent resonance condition in a transmission arrangement.
Figure 8B:
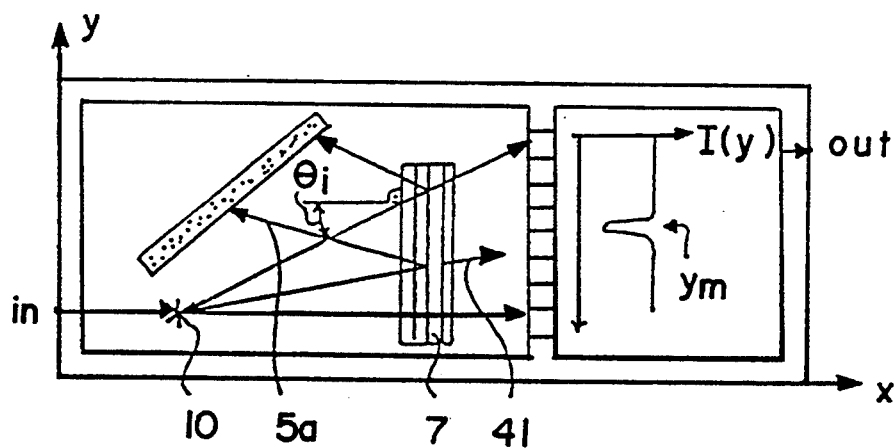
FIG. 8b shows a sensor module with a uniform Bragg grating and an angle-dependent resonance condition in a transmission arrangement.
Figure 8C:
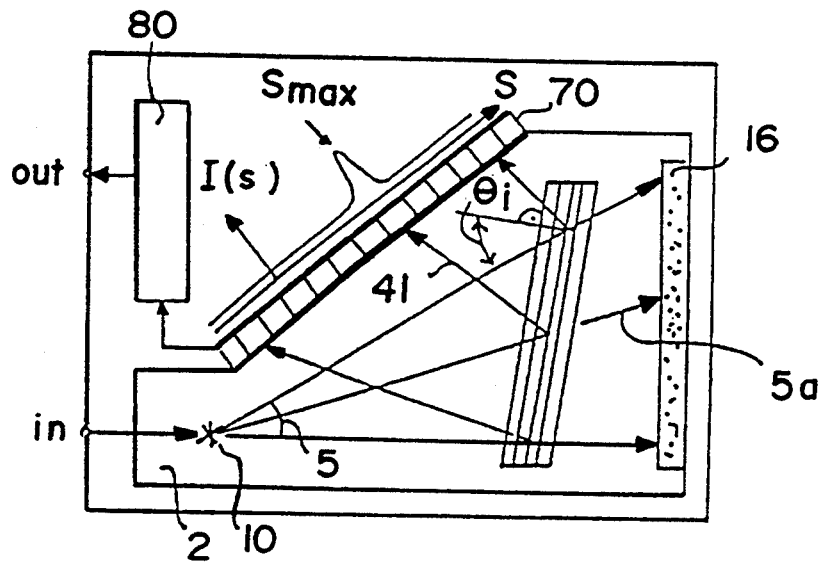
FIG. 8c shows a sensor module with a uniform Bragg grating and an angle-dependent resonance condition in a reflection arrangement.

FIGS. 8a through c schematically show exemplary embodiments of sensor modules for carrying out measuring methods that are based on a variation of the angle of incidence $\Theta$. In carrying out the measurement, the angle dependency of the resonance condition in Bragg gratings is utilized. A different value of the module parameter, in this case the resonance angle $\Theta_1$, corresponds to each value of the measuring variable 50.

In FIG. 8a, the light of a laser 10 is collimated with a lens 20 and delivered as a beam 5 to a sensor window 40, which is located above the planar waveguide 2 in a region in which a Bragg grating 13 is located. The course of the grating lines of the nonuniform grating 13 is selected such that the angle of incidence $\Theta_1$ on the grating depends on the grating y. This location-dependent angle of incidence $\Theta_1=\Theta_1(y)$ means that the resonance condition for Bragg reflection of the partial beam 5a is met at only one location $y_m$. The location $y_m$ analogously to FIGS. 3-5, depends on the value of the variable 50 to be measured in the sensor field 40. The reflected proportion 5a is destroyed in an absorber 16. As an alternative to this transmissive arrangement, a reflective arrangement may be selected, essentially by transposing the positions of the detector 70 and absorber 16.

FIG. 8b shows a variant of the module shown in FIG. 8a that makes do with a uniform grating 7 and needs no collimating optics. Here the location dependency of the angle of incidence $\Theta_1=\Theta_1(y)$ comes about by the natural divergence of the light emerging from a laser diode 10. For the method corresponding to this module and for the function of the other components, the same description as for FIG. 8a applies.

FIG. 8c shows a variant of the module of FIG. 8b, but this operates by reflection. A peak at the point $s_{max}$ of the intensity distribution I(s) at the location of the detector 70, which originates in the resonantly reflected partial beam 5a, corresponds here to the "hole" at the location $y_m$ of the intensity distribution I(y). The absorber 16 prevents interfering light resulting from the transmitted light. It is clear that it is possible to use a second detector, instead of the absorber, in order to make a sensor that is capable of meeting more stringent demands. Other arrangements may also be selected, and by way of example the light source may be additionally regulated as suggested in FIG. 2 by the lines 65 or 85.

Figure 9A:
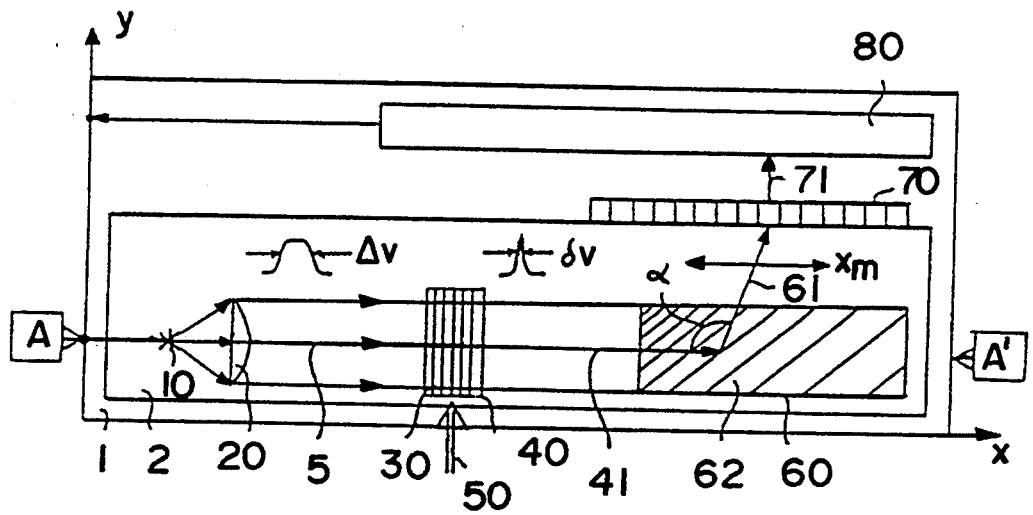
FIG. 9a shows a sensor module with a novel integrated optical filter, tunable by the measuring variable, in the sensor field.

In the exemplary embodiment of FIG. 9a, the light of the light source 10 (preferably a laser diode or light emitting diode) integrated into the waveguide 2 is collimated with a frequency bandwidth delta v by an optical element 20 and carried to the sensor field 40. A novel narrow-band optical filter 30 with a bandwidth v<delta v, which is tunable by the measuring variable 50 via a variation in the effective refractive index in the region of the Bragg grating 30, is disposed in the sensor field. This optical filter 30 may be embodied as an active, resonant-transmissive DBR filter (see [KAZO90]), by varying the optical properties of the grating region not via the control current ($I_g$ in [KAZO90]), but rather via a variation in the effective refractive index N effected by the measuring variable. Another option is to use a passive resonant-reflective filter, as in FIGS. 3–8.

In contrast to the method shown in FIGS. 3–8, for example, the measuring variable 50 here does not bring about any variation in the resonance location or resonance angle, but rather in the resonant frequency $v_r$ of the resonantly transmitted or reflected wave; that is, the module parameter here is $v_r$. The frequency range delta v of the light source 10 must in this case be adequately wide; that is, it must include at least the frequencies $v_1$ ... $v_2$ of the filter 30 corresponding to the value range $W_1$ ... $W_2$ of the measuring variable 50. The value of the module parameter is determined in an optical analyzer 60 (in this case embodied by a chirped grating 62, whose effect is described in U.S. Pat. No. 3,814,98, for example). The beam deflection angle $\alpha$ between the waves 41 and 61 may be used as a parameter for optimizing the analyzer 60 and generally is other than 90°. This is also true for FIGS. 6, 7, 10, 14, 21, and 22. The analyzer 60 converts the value of the module parameter into an intensity distribution, which has a maximum or minimum at the location $x_m$ and is delivered to the detector 70. The further processing of the resultant detector signal 71 proceeds analogously to the description of FIGS. 3–8.

Figure 9B:
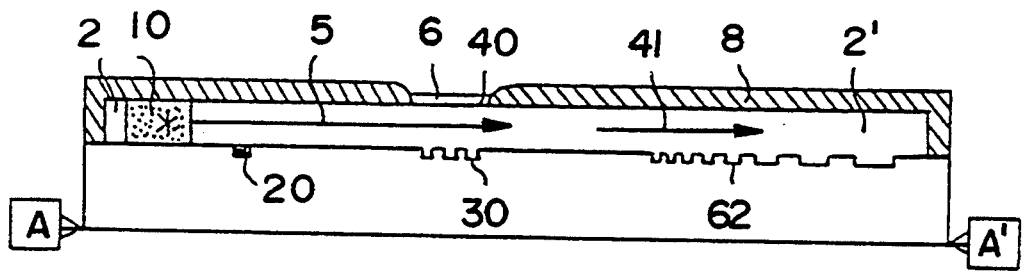

FIG. 9b shows the section A-A' of the plan view on the sensor module schematically shown in FIG. 9a. Here the laser 10 is connected directly to the waveguide 2' and the lens 20, the grating 30 disposed below the sensor field 40, and the chirped grating 62 are embodied directly in the substrate, in the form of a surface relief. An arbitrary absorber (not shown; see FIG. 7a) may also be produced in the substrate (for instance by a diffusion process). The fabrication of the "passive" waveguide part 2' such as an RLVIP film (see [KUNZ91]), can then be done after the fabrication of the components 10, 20, 30 and 62 is concluded. On the basis of a "universal structure", this affords the capability of making a great number of different sensor types, because part 2' of the waveguide, the protective layer 8 and optionally one or more sensor layers 6 can be optimized separately for the particular intended application (for instance, for the type of measuring variable and the chemical property of the ambient medium).

Figure 9C:
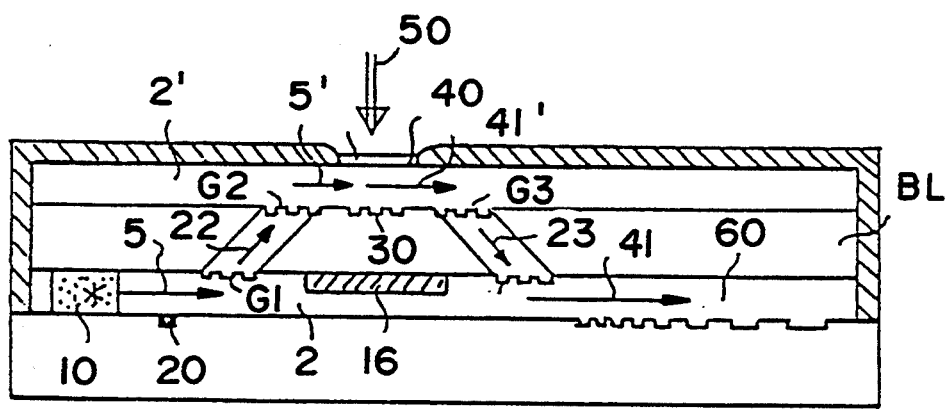
FIG. 9c shows a sensor module made by multilayer technology, with a sensor field 40 in a second waveguide 2'.

FIG. 9c shows another variant that makes it possible to create such a universal structure. Here the components 10, 20 for producing the guided wave 5 are located in a waveguide 2. With the aid of two conventional grating couplers G1 and G2 [TAMI 79, 90–101], the guided wave 5 is overcoupled to a second waveguide 2' and converted into a second guided wave 5', which now interacts with the measuring variable 50 in the sensor field 40 in the region of an optical filter 30. Once the interaction has taken place, the wave 41' is fed back into the waveguide 2 with the aid of the gratings G3 and G4 and is delivered as a wave 41 to the analyzer 60, which is also located in the waveguide 2. A buffer layer BL is located between the waveguides 2 and 2'. An absorber 16 is also located in the waveguide 2, to prevent light from the wave 5 from directly reaching the analyzer. A coupling between two waveguides disposed one above the other that is achieved with the aid of gratings is described in [CHEN91; TAMI79] ("grating- assisted coupling"), for example. The waveguides 2 and 2' may also be coupled by other methods of integrated optics; however, it is important that two different waveguides be used here. Splitting the tasks between the waveguide 2 (producing the waves and signal processing) and 2' (interaction with the measuring variable) enables optimal selection of both production technologies and waveguide materials and parameters. For a number of different applications, the same basic structure (substrate up to and with buffer layer BL) can be used. Depending on the use, then only the waveguide 2' with the gratings G2, 30, G3, the sensor layer 6 and the sensor field 40, will be selected to be different. Such a structure is somewhat more complicated, but offers more freedom in optimizing the waveguide 2' for the particular application. It is clear that on the basis of the exemplary embodiment disclosed in FIGS. 9a through c, further variants can be made; for instance, the tasks can also be split among more than two waveguides, in order to optimize materials, technologies, and costs. One such option would be to dispose the detector and electronics on a silicon substrate, with the light source and optical filter in layers III–IV located above it, and with the sensor part, made by the RLVIP technique [KUNZ91], and suitable sensor layers above or ... next to the layers III–IV. Ways to apply such additional layers include not only direct deposition but also the process known as grafting [YIYA89] and the build-up of layers on the back of the substrate, if the substrate has transparent regions.

FIGS. 10a through b show a sensor module in which the measuring variable 50 varies the time frequency v of the light source 10, and a conclusion as to the measuring variable 50 can be drawn from this variation in frequency. The module parameter here is the frequency v of the light source 10. FIG. 10b is a section along the line A-A' through the sensor module in a plan view in 10a. The arrangement is like that of FIG. 7a. However, there is the substantial difference that the sensor field 40 is located not in the region of the analyzer 60 but rather in the region of the light source 10. The light source is embodied here as a DFB laser [EBEL89, 359–63]. The measuring variable 50 here comes to interact with the guided wave 5 in the region of the active medium, for instance in that the measuring variable determines the refractive index of the sensor layer 6. As a result, the resonance condition of the DFB laser feedback and hence the frequency v of the emitted light depends on the value of the measuring variable 50. Accordingly, the measuring method comprises using a light source 10 that is tunable by the measuring variable 50 and to measure its frequency v by means of an analyzer 60. This measurement can be done in various ways. In FIG. 10a, the chirped grating 7 is used for that purpose. The function of the detector 70, the electronics 80 and the absorber 16 is the same as in FIG. 7a, for example.

FIGS. 11a through 11b show two examples of light sources which are likewise suitable for carrying out the method of FIG. 10, by replacing the DFB laser used in FIG. 10 with the laser shown in FIG. 11a having a Fabry-Perot resonator or the DBR laser proposed in FIG. 11b. These are merely examples; other laser types (such as ring lasers) may also be used, as long as they are suitable for integration and have the capability of coupling their frequency to the value of the measuring variable.

Lasers of the Fabry-Perot type substantially comprise an active medium and optionally one or more passive regions, which are disposed between two reflectors R1 and R2 [EBEL89, 301–32, 363–66]. In the known lasers, care is taken to assure that external variables, such as temperature and magnetic and electrical fields affect the frequency as little as possible. In contrast to this, in the laser 10 shown in FIG. 11a, a strong dependency of the optical properties on a parameter, that is, the measuring variable, is intentionally created in the region of the sensor field 40. One option for doing this is to embody the (passive) part of the resonator in such a way (by the selection of thermooptical, magnetooptical or electro-optical materials, for instance) that the corresponding measuring variable determines the optical length of the resonator and hence the laser frequency. Depending on the type of measuring variable, a number of other options are possible. One of them is to apply a "sensor layer" over the passive part of waveguide shown in FIG. 11a, in the region of the sensor field 40. If a chemical sensor is to be achieved, for instance, then this sensor layer is selected such that its refractive index depends on the chemical composition of the surroundings. A variation in the chemical measuring variable then causes a variation in the effective refractive index of the passive waveguide part and thus a corresponding variation in the laser frequency.

If the reflectors of the Fabry-Perot laser are replaced with Bragg gratings, the so-called DBR laser [EBEL89, 358] is the result. If only one reflector is replaced (for example, if R1 is replaced by G1 with the sensor field 40), then the measuring variable also determines the frequency v. As schematically shown in FIG. 11b, such an arrangement is also suitable for making sensors of the differential type, by disposing two sensor fields, 40, 40' in the regions of two Bragg reflectors G1 and G2. The effect of the measuring variable 50 on the resonance condition of the Bragg gratings is similar to the case of the optical filter of FIG. 9 and the DFB laser of FIG. 10; that is, the reflectors G1, G2 have resonant frequencies v1, v2, which are each dependent on the values W1, W2 of the measuring variables 50, 50'. This arrangement is distinguished by the presence of two module parameters, namely the frequencies v1 and v2. For the sake of simplicity, it will now be assumed that the same measuring variables are to be measured, although at different points, which correspond to the locations of the sensor fields 40, 40'. Logically, however, different measuring variables 50, 50' may also be measured (for instance a chemical variable in sensor field 40 and a magnetic variable in sensor field 40'). Two cases A and B should now be distinguished. If the values of the measuring variables at 40 and 40' are equal, that is, if W1=W2=W(case A), then v1=v2=v, and the laser is emitting light at the frequency v. The value W of the measuring variable is the result of the relationship v=v(W); simultaneous variations delta W in the measuring variables cause variations delta v in the frequency, which can be measured with the analyzer of FIG. 10. If the values of the measuring variables do not vary simultaneously, then W1 is <>W2 (case B); the precise effect depends on the construction of the laser. If W1 and W2 differ too greatly, or in other words if the difference W2−W1 becomes to great, then the difference v2−v1 will also be great, and the laser oscillation will cease entirely or change into superradiation, and finally the light source will function similarly to a light emitting diode. Such an arrangement is accordingly suitable for comparing variations in the measuring variable at two different points 40 and 40', by measuring the spectrum of the emitted light using the analyzer in the sensor module. This is important, for instance if one seeks to check whether the chemical composition of a liquid is homogeneous, or whether it exhibits a gradient between the points 40 and 40'.

Figure 12A:
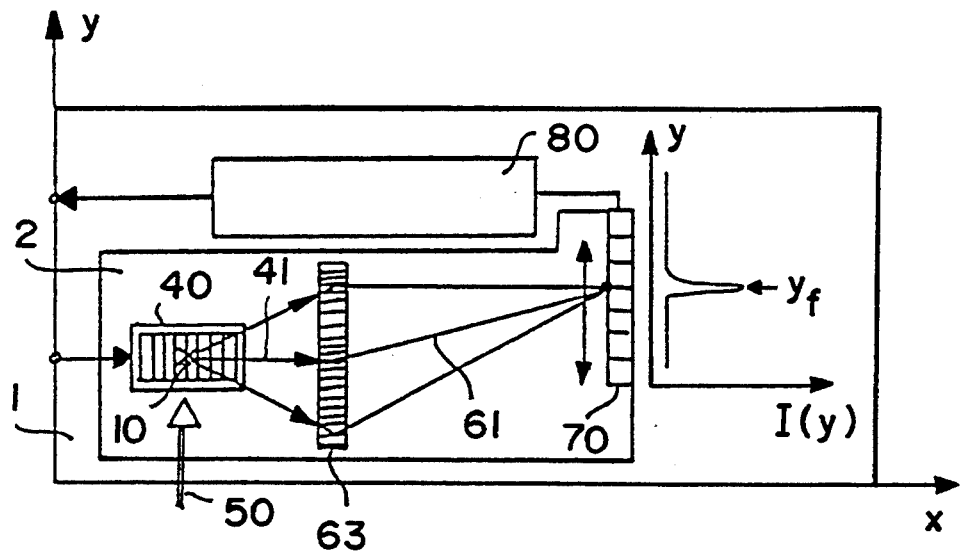
FIG. 12a shows a sensor module with a tunable light source and frequency-dependent optical imaging.
Figure 12C:
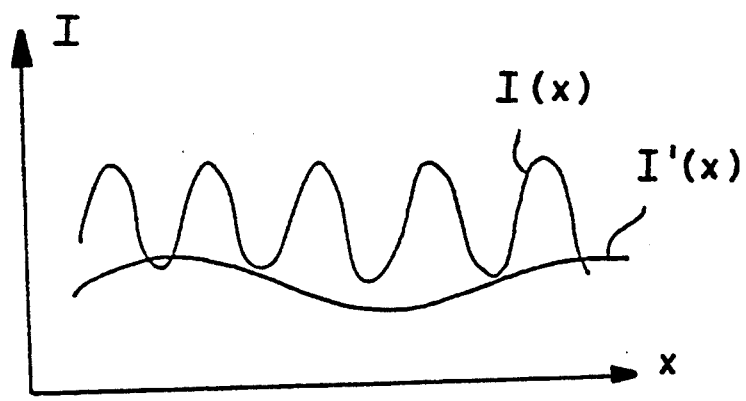
FIG. 12c is a schematic illustration of the distributions of intensity I(x) without and I'(x) with a mask in front of the detector 70 of FIG. 12b.
Figure 12B:
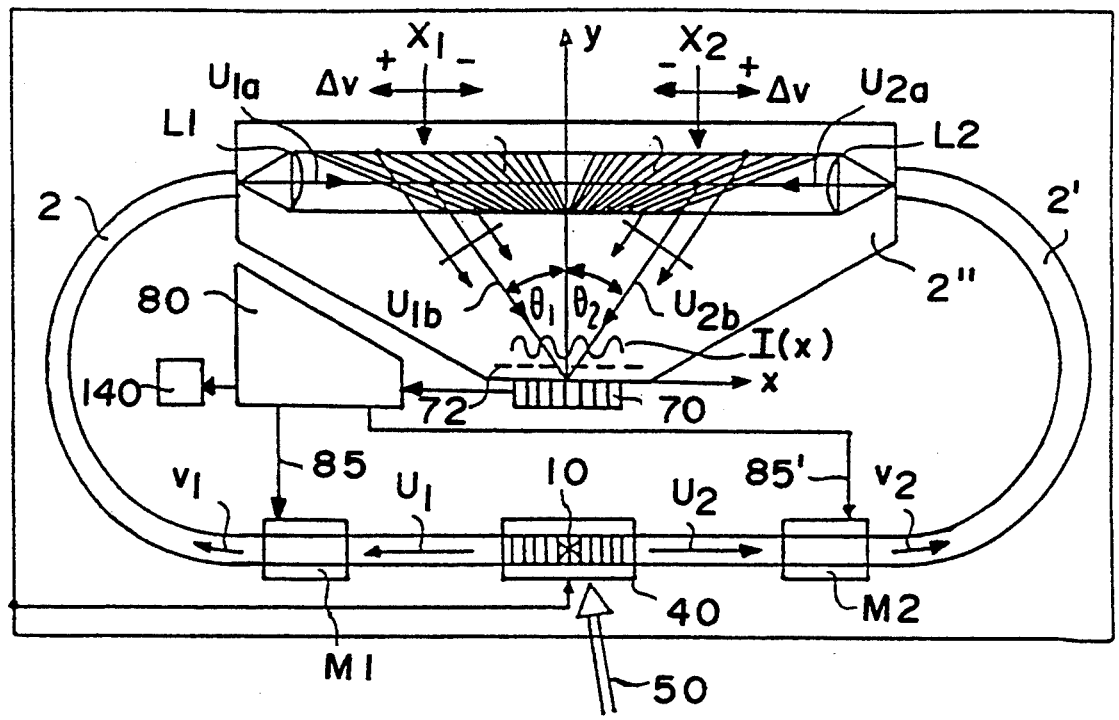
FIG. 12b shows a sensor module with a tunable light source and frequency-dependent dual-beam interference.

FIGS. 12a through 12b show two variants of the sensor module of FIG. 10, in which the measuring variable 50 likewise varies the time frequency v of the light source 10, and a conclusion as to the measuring variable can be drawn from this variation in the frequency. For the light source, the same description as that for FIGS. 10 and 11 applies. The difference here is in the embodiment of the analyzer. The analyzer comprises only the grating lens 63 [URA.90], which focuses the (divergent) guided wave 41, radiated into a planar waveguide 2, onto a detector 70. The location $y_f$ of the focus of such a grating lens, or the intensity distribution I(y) at the location of the detector 70, depends on the frequency of the light. The method is now based on determining the position $y_f$ of the focus, which is dependent on the module parameter v and hence on the value of the measuring variable 50, with the aid of the detector 70 and the evaluation unit 80 and from that to draw a conclusion as to the value of the measuring variable 50. Instead of the laser 10 shown, other arrangements for producing the wave 41 may also be used, such as the combination of components 10, 20, 30 and 40 shown in FIG. 9. The wave 41 need not have any specialized wave front, since the grating lens 63 can be designed accordingly. Other integrated optical components that permit determining the frequency of a guided wave may also be used instead of the grating lens. Such components have been described above all in connection with communications technology, where it is important to transmit many channels by so-called wavelength multiplexing [HUTC87, 35; EBEL89, 151 to 157].

The variant shown in FIG. 12b uses a kind of "dual-beam interference of guided waves", in order to measure the variation in the frequency v effected by the measuring variable 50. To that end, two guided waves u1 and u2 at frequencies v1 and v2 are used and delivered in two separate strip waveguides 2 and 2' to the analyzer, which is embodied in a planar waveguide 2". For a first method, the modulators M1 and M2 are not used; that is, v1=v2=v. In the analyzers, the waves u1 and u2 are fanned out with the aid of the optics L1 and L2 and collimated (u1a and u2a). They then strike two chirped gratings G1 and G2 and are guided by them as waves u1b and u2b to the detector 70 at the angle Θ1 and Θ2. The effect of the G1 and G2 gratings is similar to that described for FIGS. 6, 7 and 9, but the grating structure here is more complicated. The gratings G1 and G2 may be considered to be diffractive-optical elements, which produce the waves u1b and u2b in such a way that both the positions x1(b1) and x2(b2) and the angles Θ1(v1) and Θ2(v2) are defined by the frequencies v1 and v2. The wave fronts of u1b and u2b are selected such that their interference at the location of the detector 70 produces an intensity distribution I(x) from which the value of the measuring variable can be ascertained accurately and easily with the aid of the signal processing unit 80. Planar wave fronts and periodic, for instance sinusoidal, intensity distributions I(x) are preferred. The value of the measuring variable results from the periodicity of I(x), because the latter, in a known manner, is dependent on the angles Θ1(v1) and Θ2(v2).

In the event that the angles Θ1(v1) and Θ2(v2) are small and the detector has high resolution, then direct measurement of I(x) is possible. In other cases, the methods known from discreet optics for measuring I(x) with increased resolution are recommended. For instance, a mask 72 or a grating may be integrated in front of the detector 70 in such a way that a moiré pattern I'(x) [GLAT88] results in the detector, and this pattern is coarser than I(x) and reacts very sensitively to small variations in the value of the measuring variable (see FIG. 12c).

Another option is to shift the frequency of the waves u1 and u2 with the aid of modulators M1 and M2 [HUNS84, 120-157, 280-281; TAMI79, 167-194], so that v1 becomes unequal to v2. This is done via the signal lines 85 and 85' and the result is that now the intensity distribution I(x) is no longer stationary but instead starts to "run"; that is, a time-dependent intensity distribution I(x, t) results. The time dependency I(t) can be measured at a fixed point x with the aid of a simple, spot-shaped detector (or with the aid of a pin diaphragm). The measuring variable is then the result of the course I(t) analogously to the case discussed before, in which I(x) was measured.

Figure 13:
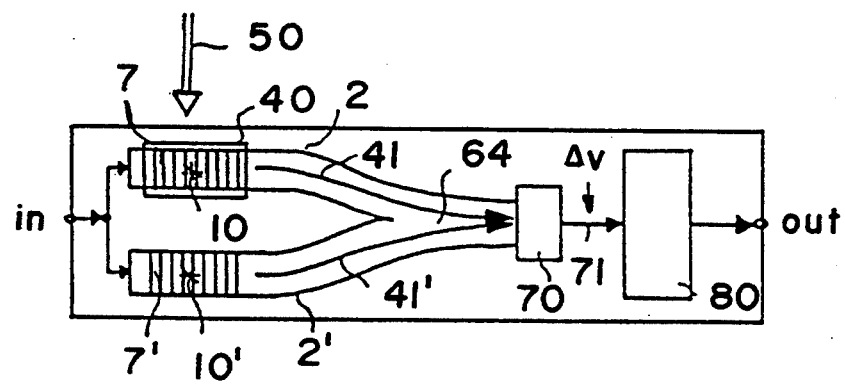
FIG. 13 shows a sensor module with a tunable light source and optical heterodyne detection.

FIG. 13 shows an exemplary embodiment that is based on optical heterodyne detection [EBEL89, 406–407]. The components essential to carrying out this method are shown schematically and include a light source 10, tunable by the measuring variable 50 and having a variable frequency v (see FIGS. 9, 10, 11), a second light source of fixed frequency v' in the form of a local oscillator 10', a so-called Y branch 64, a detector 70, and an evaluation unit 80. The module parameter here is the frequency v. The Y branch 64 may be imagined as part of a directional coupler (see [EBEL89, 141-147, 455], for example). The method then comprises causing the waves 41, emerging from the sensor field 40, and whose frequency v(W) depends on the value W of the measuring variable 50, to interfere with or be superimposed on the wave 41', generated by the local oscillator 10' at the frequency v', at the location of the detector 70. Because of the nonlinearity of the detection process, the differential signal 71 delta v=v(W)−v' of the frequencies v(W) and v' of the light amplitudes of the waves 41 and 41' is available at the output of the detector. The value W of the measuring variable or its variations can now be determined on the basis of the relationship v(W)=delta v+v' and the known or fixed frequencies v' by means of the evaluation unit 80. Other measuring branches (not shown here) with sensor fields 40, 40a, . . . may also be used; the corresponding waves 41, 41a, are then mixed by multiplexing or simultaneously with the local oscillator wave 41'. In the latter case, the measured values W, Wa, . . . can be distinguished from one another because the frequencies v, va, . . . are located in frequency bands that are characteristic for their particular sensor field.

In this sensor type as well, a differential sensor with one or more sensor fields (see FIG. 11b) can be made. The simplest option is to dispense with the local oscillator 10' and instead to use a second light source, controlled by the measuring variable, having a frequency v'=v'(W'). The frequency difference delta v=v(W)−v'(W') then provides information directly as to the difference W−W' of the values W and W' of the measuring variables.

Figure 14A:
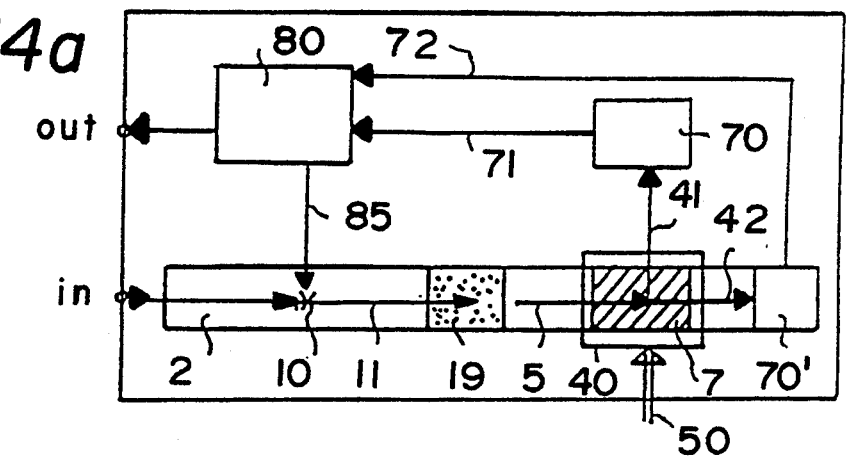
FIG. 14a shows a sensor module with a regulated light source and a resonant-reflective frequency-dependent beam splitter.

FIG. 14a shows an exemplary embodiment in which an (electrically) tunable light source 10 is used, which radiates a guided wave 11 at a selectable frequency v into a strip waveguide 2. To avoid interfering reflections, an isolator 19 may be provided [HEMM90]. Downstream of the isolator, the wave 5 meets the uniform Bragg grating 7 in the sensor field 40. If the frequency v matches the resonant frequency v1 of the grating, then the majority of the light energy from the guided wave 5 is reflected into the beam 41 and strikes the detector 70. The transmitted portion of the light strikes the detector 70' in the form of a beam 42. If the value W of the measuring variable 50 varies at the location of the sensor field 40, then this causes a shift delta v1 of the resonant frequency v1 of the grating 7. The way in which the shift in the resonance condition at gratings functions by means of a measuring variable has been described in FIGS. 9 through 11. The module parameter here is the frequency v1. If the frequency v is kept fixed, the result is a continuation of the beam 41 and a simultaneous increase in 42. Variations delta W in the value W of the measuring variable can now be measured, for instance in the evaluation unit by determining the quotient $$Q(w) = L41/L42 = (\text{SIGNAL } 71)/(\text{SIGNAL } 72)$$

of the powers L41 and L42 striking the detectors 70 and 70'. This is a first mode of operation, in which a tunable light source is not needed, or no tuning takes place.

In a second mode of operation, a closed-loop control signal 85 is generated in the evaluation unit 80, and with its aid, the frequency v of the light source is regulated in such a way that v always equals v1(W); that is, v follows the measuring-variable-dependent grating resonant frequency v1(W). This is equivalent to regulation to a maximum value of the quotient Q(w). To increase the accuracy and/or lengthen the service life of the sensor module, the other operating parameters (for instance operating voltage or current) of the light source may additionally be regulated as well.

Figure 14B:
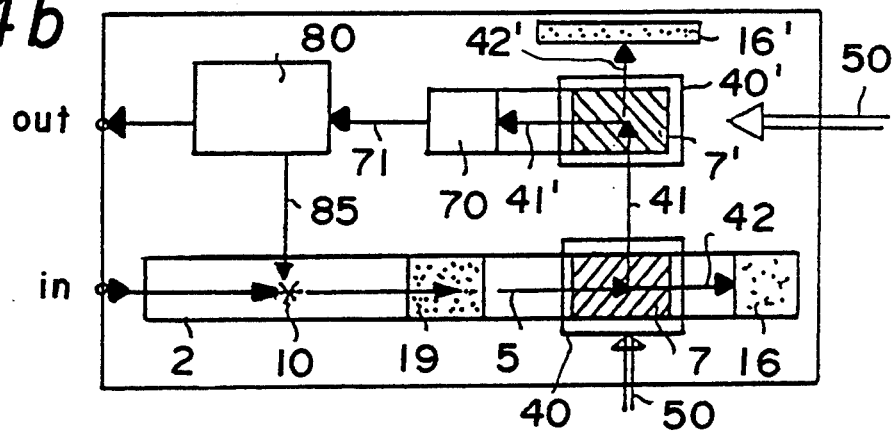
FIG. 14b shows a sensor module with a regulated light source and two resonant-reflective frequency-dependent beam splitters 7 and 7' with sensor fields 40 and 40'.

FIG. 14b shows a variant of the arrangement of FIG. 14a, in which two sensor fields 40 and 40' and two gratings 7, 7' are present as well. The other components may be selected to be the same as in FIG. 14a, but here a simpler arrangement is shown, in which the detector 70' has been replaced by an absorber 16 (see FIGS. 7, 10). The function of the components from the light source 10 to the optical output 41 is the same as in the description of FIG. 14a. Here, the wave 41 reflected at the grating 47 strikes a second grating 7' where part of it is transmitted as a wave 42 to the absorber 16' and part is transmitted as a wave 41' to the detector 70. Similarly to the description of FIG. 11b, a differential arrangement of this kind has advantages for certain applications, because deviations in the measuring variables at the location of the fields 40 and 40' can be ascertained very sensitively. For the sake of simplicity, we will discuss here only the case of a measuring variable whose values W1, W2 are to be measured or compared at the points 40, 40'. We also assume that for W1=W2 the resonant frequencies v and v' of the gratings 7 and 7' are to be the same. The expansion to the cases of various measuring variables, various sensor fields and more than two interlinked sensor fields, which are likewise of great interest, is easy to do for one skilled in the art and will not be discussed here. In any case, the module parameters are the frequencies v and v'.

Figure 14C:
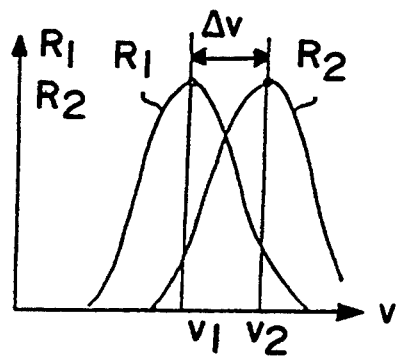
FIG. 14c is an explanatory diagram for 14b showing resonance curves.
Figure 14D:
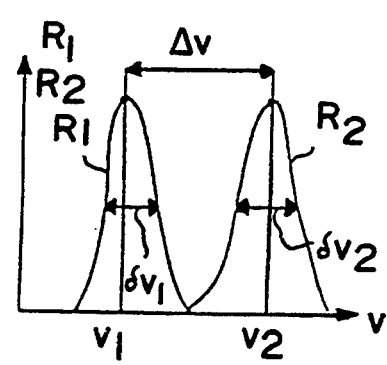
FIG. 14d is an explanatory diagram for 14b showing resonance curves.

On the above assumptions, deviations delta W=W1−W2 in the measuring variable have the effect that the resonant frequencies v1 and v2 have a corresponding deviation delta v=v1−v2. If the differences in delta W or delta v overlap, then the resonant curves of the spectral reflection capacity R1(v) and R2(v) of the gratings 7 and 7' overlap strongly as shown in FIG. 14c. If the differences are major, that is if the difference delta v becomes greater than the widths $\delta v1$ and $\delta v2$ of the resonance curves R1(v) and R2(v), then the curves overlap only slightly (see paragraph 14d). The result is that the shape and height of the curve of the resultant total spectral reflection capacity $R_T(v)=R1(v)\cdot R2(v)$ depend on the difference delta W in the measuring variable at 40 and 40'. The course of the function $R_T(v)$ and thus the gradient of the measuring variable 50 in the region of the sensor fields 40, 40' can be determined by the evaluation and control unit 80 with the aid of the tunable light source 10. To that end, the control unit varies the frequency v as the light source via the signal 85 and in so doing measures the detector signal 71 corresponding to the function $R_T(v)$. If the measuring variable at 40 and 40' varies in the same way, then the result is merely a shift in the resonance curve without a change in shape, from which the synchronized variation in the measuring variable can be determined. Other modes of operation are possible, by regulating the frequency v to a predetermined state, instead of varying it, (for example, the maximum value of $R_T$ and measurement of this value) and/or the absorbers are replaced by detectors and their signals are used to determine the measuring variables or to regulate and/or stabilize the sensor.

Figure 15A:
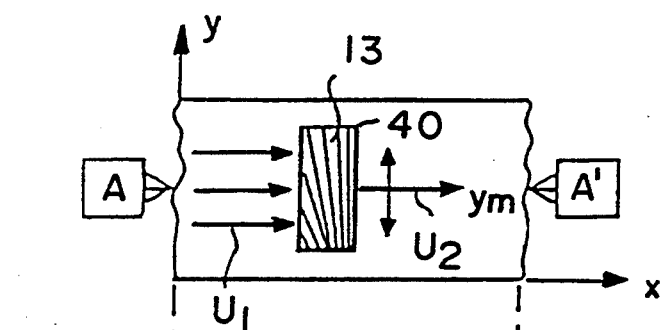
FIG. 15a shows a novel element for location-dependent overcoupling via transverse-damped waves between two waveguides, in a plan view.
Figure 15B:
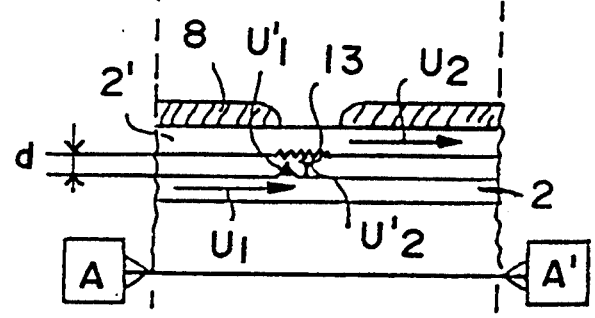
Figure 15C:
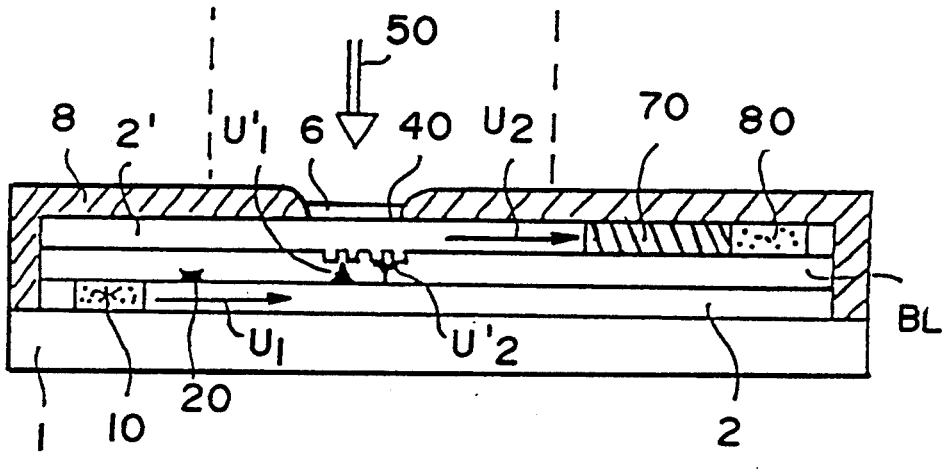
FIG. 15c is a section through a complete sensor module with an element of FIGS. 15a and 15b.

FIGS. 15a through c show an exemplary embodiment which uses a novel element for location-dependent coupling between two waveguides disposed one above the other. The determination of the measuring variable is done analogously to the description of FIG. 5, but instead of a Bragg grating, a novel, nonuniform grating coupler is used to generate the location-dependent resonance condition; it enables a location-dependent overcoupling via transversely damped waves of the waveguide 2 into a waveguide 2'. The sensor field 40 with an arbitrary sensor layer 6 is located in the coupling range of this grating 13. The coupling of the guided waves u1 and u2 is effected via their transverse-damped portions u1' and u2' in the buffer layer BL. This method can be called chirped grating-assisted coupling, in analogy with the usual grating-assisted coupling [CHEN91]. Via the thickness d of the buffer layer BL, the coupling efficiency can be adjusted; d is typically less than the wavelength of the light.

Figure 16A:
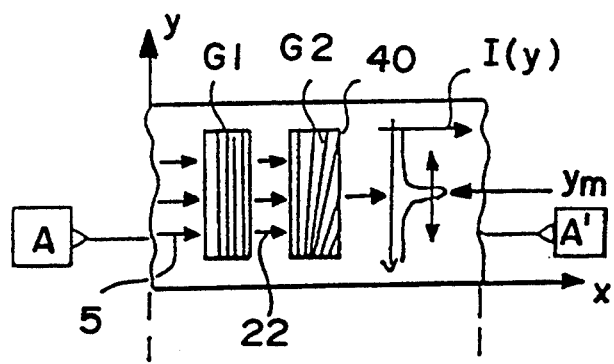
FIG. 16a shows a novel element for location-dependent overcoupling via radiating waves between two waveguides, in a plan view.
Figure 16B:
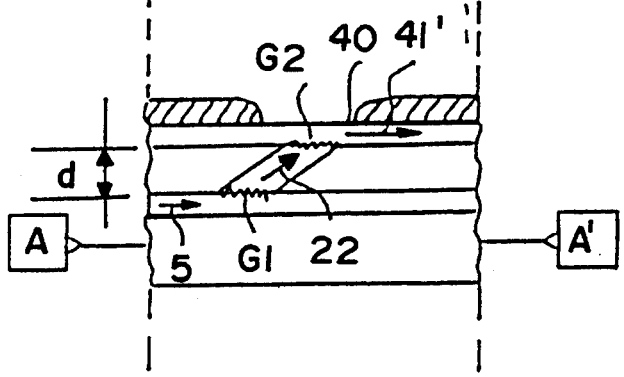
Figure 16C:
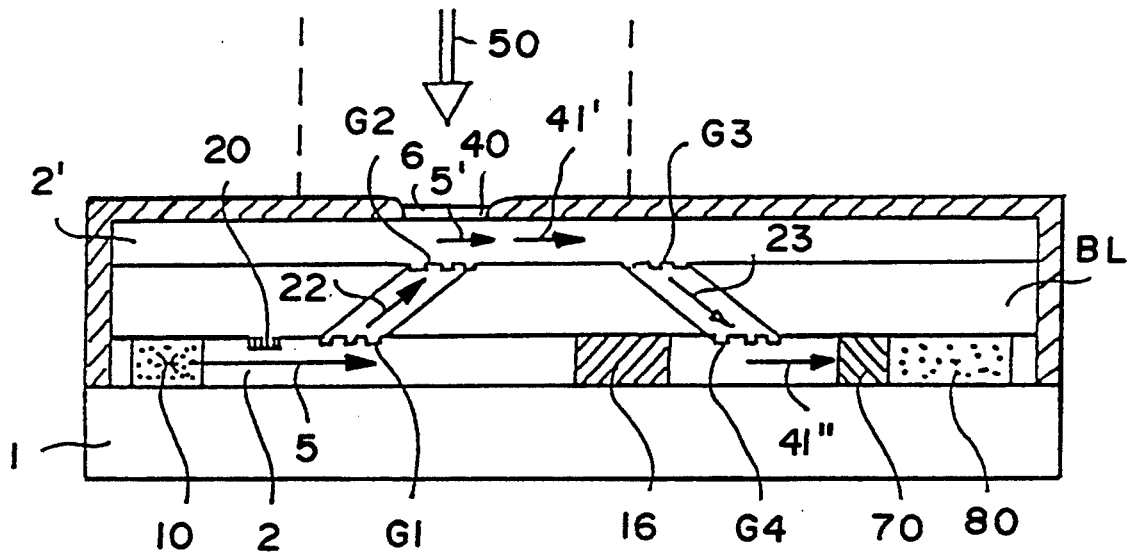
FIG. 16c is a section through a complete sensor module with an element of FIGS. 16a and 16b.

In contrast to the arrangement of FIG. 5, meeting the resonance condition here effects a maximum in intensity at the point $y_m$ of the wave u2 striking the detector or of the power transmitted to the waveguide 2'. The module parameter is the location $y_m$. Otherwise, the same description logically applies as for FIG. 5; here, the value of the measuring variable is determined on the basis of the maximum, instead of the minimum, at $y_m$. Although the arrangement shown here takes more space than that of FIG. 9 (at least in the Y direction), nevertheless it is easier to fabricate in the current state of the art (simple components, minimum number). The coupling element shown in FIGS. 15a and 15b can be used in various ways; instead of the arrangement of FIG. 15c, for instance, the wave u2, once interaction with the measuring variable 50 has taken place, can also be fed back into the waveguide 2 (with the aid of the conventional grating-assisted coupling). The detector in the evaluation unit could then also be located at the level of the waveguide 2 or in the substrate, as described in further detail in FIG. 16c.

The action of the aforementioned coupling element can also be achieved in other ways. For instance, instead of a non-uniform grating 13, a nonuniform waveguide 2' and/or a nonuniform buffer layer BL may be used, for instance. On this point, see also the alternatives of FIGS. 3–5 for achieving a location-dependent resonance condition by means of gradients in thickness and/or refractive index.

FIG. 16 shows a sensor module related to the arrangement of FIG. 15. The coupling takes place here via the radiating waves 22 and 23, rather than via transverse-damped waves. The gratings G1, G3 and G4 are typical grating couplers, while G2 represents a novel grating coupler, in which the periodicity varies locally transversely to the direction of incidence of the radiating wave (this is known as a chirped input coupler). As a result, the intensity of the wave 5' overcoupled into the waveguide 2' becomes high only at the point $y_m$ at which the resonance condition for the coupling in is met. The module parameter here is the location $y_m$. This resonance condition is fixed by the interaction of the wave 5' with the measuring variable 50 in the sensor field 40, in analogy with the descriptions of FIGS. 3–5; the resonance condition now fixes not the location of maximum Bragg reflection but rather the location of maximum overcoupling. Instead of an input coupler, an output coupler may also be used; the arrangement can be obtained from FIG. 16c, by having the elements 10 and 20 change places with the elements 70 and 80 and by reversing the direction of the waves 5, 22, 5', 41', 23 and 41". However, the situation is not precisely reciprocal, since the output coupling will generally be effected over the entire range of the output coupling grating G2; the angular distribution is now location-dependent and depends on the measuring variable. The actual discrimination then takes place in the following input coupler, in that coupling back from the waveguide 2' into the waveguide 2 can be done only at a certain angle. A maximum in intensity that is dependent on the measuring variable is again produced at the detector.

Figure 16D:
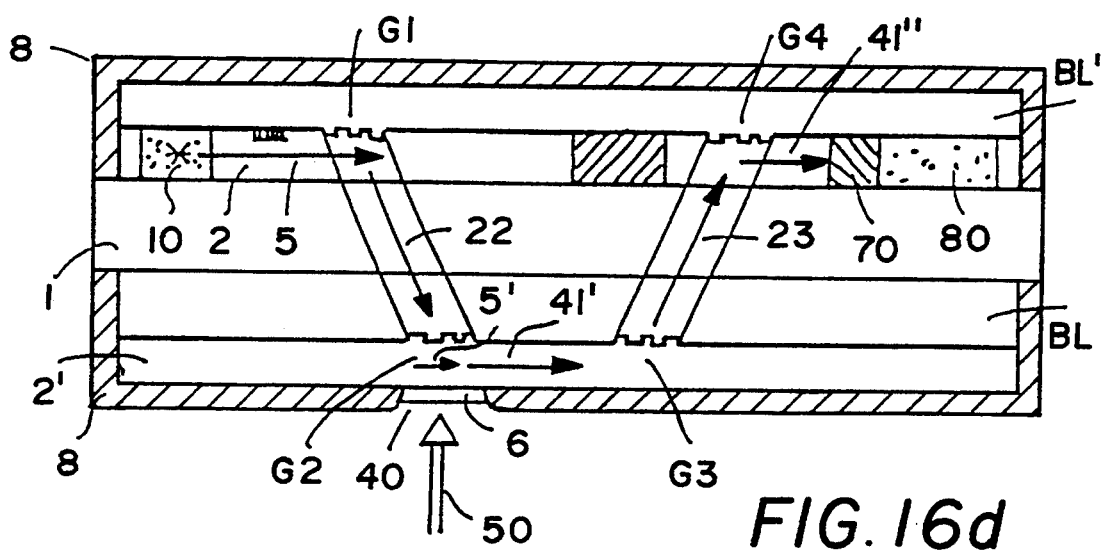
FIG. 16d is a section through a complete sensor module with an element of FIGS. 16a and 16b with a sensor part on the back of the substrate.

Since in this arrangement the coupling between the waveguides 2 and 2∝ is effected by radiating waves, the thickness d of the buffer layer BL can be selected practically arbitrarily. This has advantages for applications in which sensitive elements on the substrate (such as the light source 10 and electronics 80) should be additionally protected by a thick layer BL, for instance in cases where harmful substances could diffuse in via the sensor field because of an aggressive chemical environment. In cases where a substrate transparent to the radiation of the light source 10 can be used, there is a further option of producing the components 10, 2, 20, G1, 16, G4, 70, 80 on one side of the substrate and the sensor part on the other side, as shown in FIG. 16d. The waves 22 and 23 here pass through the substrate 1. An additional buffer layer BL', which is completely covered by a protective layer 8, is applied over the waveguide 2.

Figure 17A:
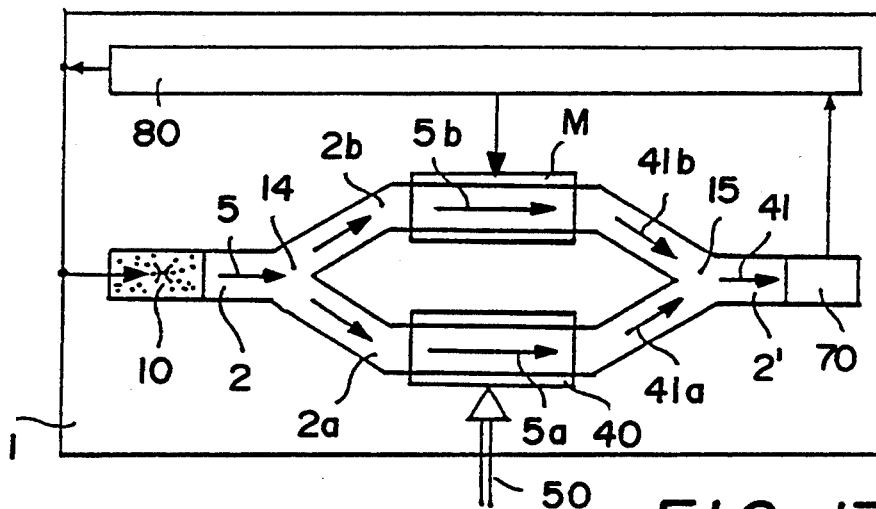
FIG. 17a shows a sensor module with a phase as a module parameter and Mach-Zehnder interferometer with a modulator M for determining it.
Figure 17B:
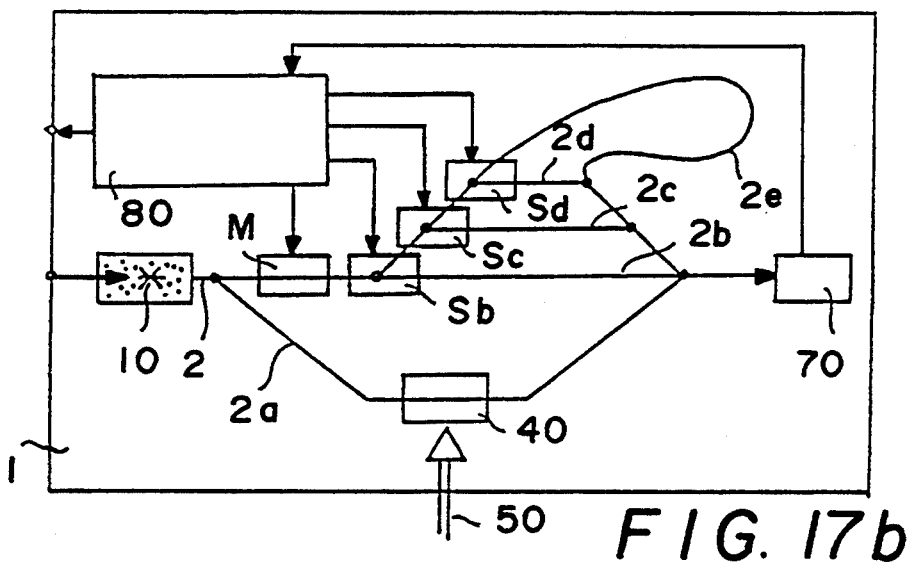
FIG. 17b shows a variant of 17a with reversible reference arms.

FIGS. 17a–b show two exemplary embodiments in which the module parameter, in this case the phase of the guided wave, is measured with the aid of simple integrated optical interferometers. In the method of FIG. 17a, a narrow-band light source 10 produces a guided wave 5 in the strip waveguide 2. This wave meets a Y branch 14, and the light streams split off to the waveguides 2a and 2b. The sensor field 40, in which the effective refractive index $N_a$ is influenced by the measuring variable 50, is located in the waveguide 2a. As a result, the wave 5a' in the waveguide 2a undergoes a phase shift delta $\phi_a$ compared with the wave 5b' in the waveguide 2b, in which in the simplest case the effective refractive index $N_b$ is constant. By means of a second Y branch 15, the waves 41a and 41b from the waveguides 2a and 2b are coherently superimposed, or in other words made to interfere, in the waveguide 2' to make a wave 41. Combining two Y branches in this way makes a Mach-Zehnder interferometer, which as an individual component has been known for a long time [DAKI88, 305]. In the method of FIG. 17a, the value of the measuring variable 50 is determined via the phase variation delta $\phi_a$, and the corresponding power of the guided wave 2' is determined with the aid of the detector 70 and the signal processing unit 80.

In principle, no modulator M is necessary—but in practice the performance of the sensor module can be considerably increased by introducing a controlled phase shift delta $\phi_b$ in the reference arm 2b by means of a modulator M. The operating point of the sensor module can therefore be located in a sensitive region and/or, by varying delta $\phi_b$, not only the magnitude but also the direction of a variation in a value of the module parameter and thus of the measuring variable can be determined with high accuracy. Various types can be used as the modulator; for instance, see [HUTC87, 190-207].

Unfortunately, if a typical modulator is used the typical material parameters often do not allow the optical travel length and hence the phase shift delta $\phi_b$ to be varied sufficiently strongly in a simple way. It can be done, however, with a method corresponding to FIG. 17b. While the measuring arm 2a of the interferometer is embodied analogously to FIG. 17a, the integrated optical switches Sb, Sc and Sd ([HUTC87, 261, among others) make it possible to incorporate the segments of the strip waveguides 2b, 2c, 2d and 2e selectively into the reference arm. The strip waveguides here are shown only as lines. The selection of the optical length of these segments makes it possible to select various measuring regions within which the operating point—as described above—can be finely tuned with the modulator M.

The arrangement of FIG. 17b makes it possible to employ other, extremely valuable and sensitive methods for the sensor system which nevertheless demand major variations in optical travel lengths or transit times. Such methods include so-called white light interferometry and optical time domain reflectometry (OTDR) methods [TAKA90]. White light interferometry uses a wideband light source with a short coherence length, in order to detect the state of equal phase shifts in the reference and measuring arms. Its important advantages are that not merely variations but also the absolute value of the measuring variable can be determined with it, and no recalibration is necessary, for instance in electrically supplied sensor modules and in the event of a power failure. The signal processing unit 80 determines the value of the measuring variable on the basis of the variation in the detector signal as a function of the control signals for the modulator M and the switches Sb, Sc and Sd.

Naturally a number of segments 2b, 2c, 2d, ... with corresponding switches Sb, Sc, Sd, ... may be used to expand the measuring range, and/or together with a plurality of measuring arms, to measure a plurality of measuring variables in parallel. The measuring arms may also be provided with switches, or given suitable dimensioning may also be connected simultaneously to the waveguide segments 2 and 2' (multiplexing mode).

To carry out the above-described methods, other interferometer types may also be used, if they are suitable for integration. Examples are the Michelson interferometer, but also many of those shown in [BORN80].

Figure 18A:
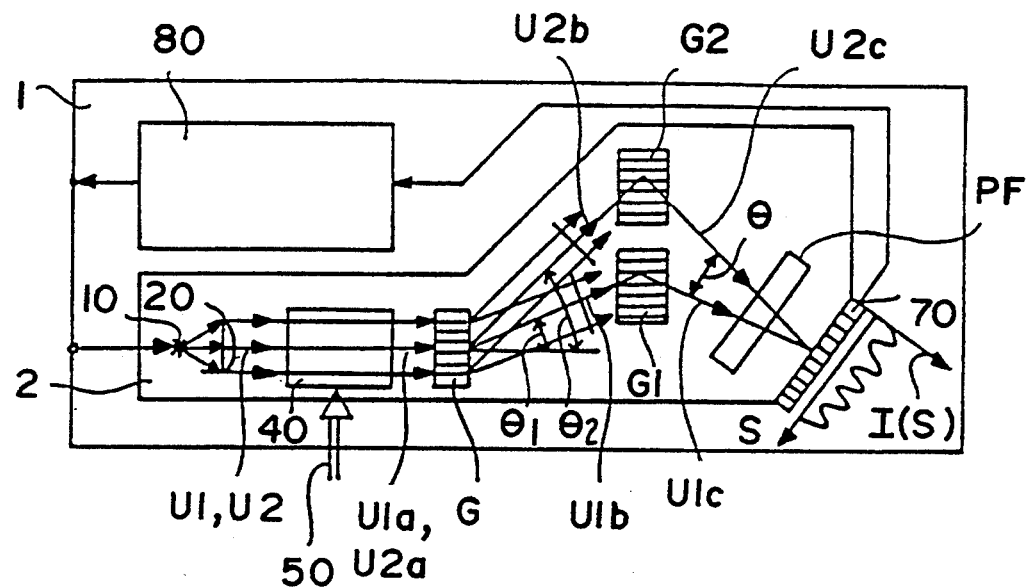
FIG. 18a shows a sensor module with two waves in the sensor field whose phase difference is measured with the aid of an interference arrangement.
Figure 18B:
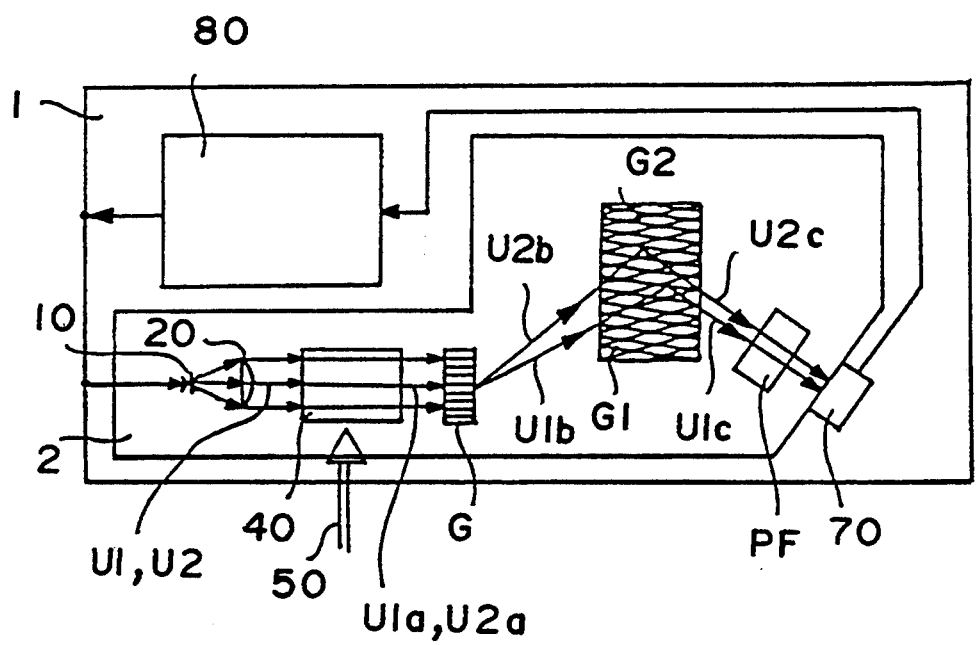
FIG. 18b shows a variant of FIG. 18a that makes due with a single detector.

FIGS. 18a–b show two exemplary embodiments, in which the measuring variable simultaneously effects various phase shifts PHI1, PHI2 for arbitrarily selectable modes u1, u2, particularly having different polarizations. In FIG. 18a, a quasi-monochromatic light source 10 and a collimating optical element 20 are used to excite two modes u1 and u2 simultaneously. It is known [TAMI79, 13–81] that modes of different polarization and/or order undergo, among other effects, a different variation in their phase velocity or effective refractive index N, if at least one waveguide parameter (such as the film refractive index or film thickness) is varied. By a suitable selection of the modes and waveguide parameters, it can be attained that a variation in the value of the measuring variable 50 effects the greatest possible variation in the difference delta N=delta N1−delta N2 between the variations of the effective refractive indexes N1(u1) and N2(u2) of the two modes inside the sensor field. The modes u1a and u2a emerging from the sensor field accordingly have a phase difference delta $\phi_a$, which depends on the value of the measuring variable. The module parameter here is the phase difference delta $\phi_a$. This effect has long been known and is also utilized in International Patent Application WO 89/07,756. While International Patent Application WO 89/07,756 utilizes a complicated and expensive optical system outside the waveguide in order to measure this phase difference, however, a method and an apparatus are disclosed here that make it possible to perform the evaluation within the waveguide 2 itself. To that end, at a diffraction grating G, the modes u1a and u2a are diffracted in the form of waves u1b and u2b in different directions Θ1 and Θ2; they then strike two further gratings G1 and G2, where they are diffracted again. This produces at least two waves u1c and u2c, which are made to interfere at an intermediate angle Θ at the detector 70, resulting in an intensity distribution I(s). For the sake of simplicity, only the central beam (u1c, u2c) is shown, instead of the expanded beam cluster.

If modes having the same polarization are involved, and if only the two modes u1c and u2c are generated, then filtration can be dispensed with, and at the detector, an intensity distribution I(s) is created, from which the variation in the measuring variable can be determined. This method is based on the fact that the grating diffraction is a coherent process, and that the effective refractive index depends on the measuring variable only in the region of the sensor field. The angles Θ1, Θ2 and Θ are therefore independent of the measuring variable, while the phase difference delta $\phi_c$ between u1c and u2c is rigidly coupled to the difference delta $\phi_a$. It can be seen from this that a variation in the measuring variable effects a variation of delta $\phi_c$ and hence substantially effects a shift in the intensity distribution I(s) to I(s+-delta s). This shift delta s is measured with the aid of the detector 70 and the signal processing unit 80, and the corresponding variation in the measuring variable is determined from that.

If the modes u1 and u2 have different polarization (for instance, $TE_0$, $TM_0$), then they cannot be made to interfere directly. However, it is possible to allow the waves u1b and u2b to strike Bragg gratings in such a way that a plurality of modes are produced (mode mixing), and two of them are identically polarized; for instance u1c and u2c are both $TE_0$. By filtration, for instance with a so-called plasmon filter PF, undesirable modes can be filtered out, so that once again two modes u1c and u2c having the same polarization can be made to interfere at the detector. Technical details on mode mixing and on the plasmon filter can be found in [GALE89; VOIR89], for instance.

FIG. 18 shows a variant of FIG. 18a, in which the gratings G1 and G2 are superimposed and the waves u1c and u2c strike the detector colinearly; that is, the angle Θ of FIG. 18a is equal to zero. This allows the use of a single detector instead of the detector array shown in FIG. 18a. The phase shift delta $\phi_c$ between u1c and u2c here causes a variation in the power striking the detector, from which a conclusion as to the measuring variable can be drawn. It is not essential that the gratings be superimposed; they may also exist at separate points. However, it is important that the gratings be selected such that the grating G1 does not interfere with the diffraction of the wave u2, and the grating G2 does not interfere with that of the wave u1. Otherwise the method works as described for FIG. 18a. Once again, the module parameter is the phase difference delta $\phi_a$ of the modes u1a and u2a emerging from the sensor field 40.

Figure 19:
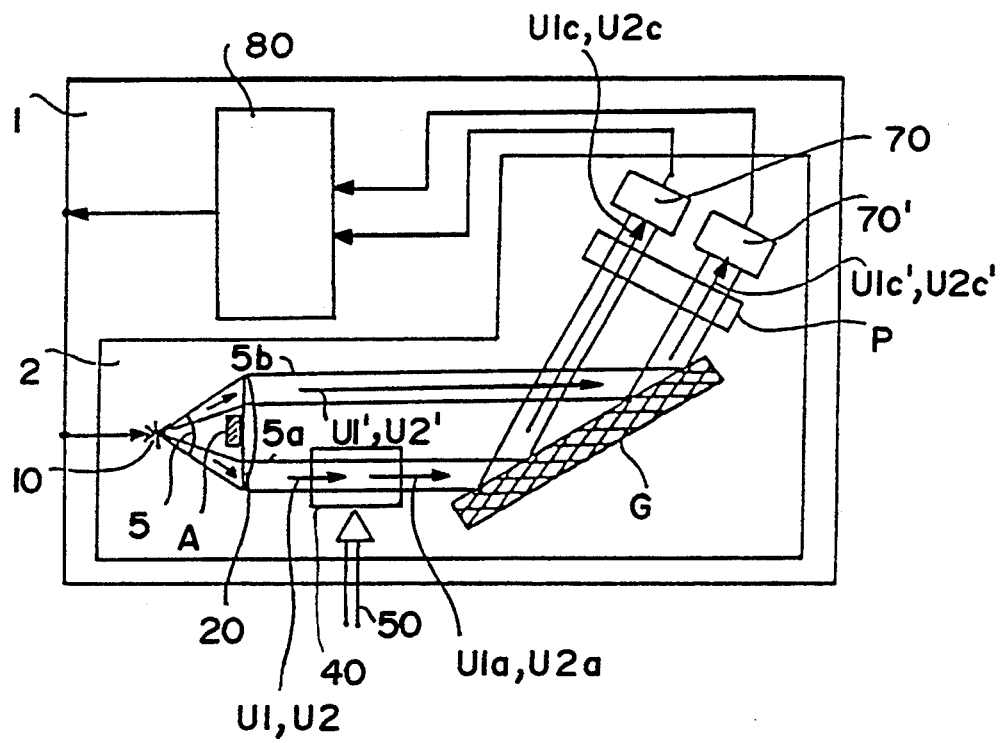
FIG. 19 shows a sensor module with two waves in the sensor field and two reference waves, whose phase differences are measured with the aid of interference arrangements.

FIG. 19 shows an exemplary embodiment in which the light originating in the light source 10 is split, with the aid of a diaphragm A and a collimating optical element 20 are split in the same waveguide 2 into a reference beam 5b and a measuring beam 5a, which will be referred to below as the reference and measuring channel. As in FIGS. 18a–b, once again there are two different guided waves u1 and u2, on the one hand, and u1' and u2' on the other, in each "channel"; that is, the measuring channel 5a corresponds to FIGS. 18a–b, while the reference channel 5b is additionally present. Once again, the module parameter is the phase difference delta $\phi_a$ of the modes u1a and u2a emerging from the sensor field 40. Depending on how the grating G is embodied, either a striped pattern (see I(s) in FIG. 18a) or a variation in power as in FIG. 18b is produced at the location of the detectors. The function of the polarization filter P is the same as that in FIGS. 18a–b or in [GALE89]. The drawing is kept very schematic; depending on the situation, still more components may be necessary in order to cause the waves u1c, u2c, and u1c', u2c', which are respectively carried to the detectors 70 and 70', to interfere with one another The advantage of a reference channel is that phase shifts that do not originate in the measuring variable but instead occur as a result of temperature changes can be measured in both channels and corrected in this way. This is important for precision sensors with high measuring accuracy and good long-term stability, for such applications as industrial process control and medicine.

Figure 20:
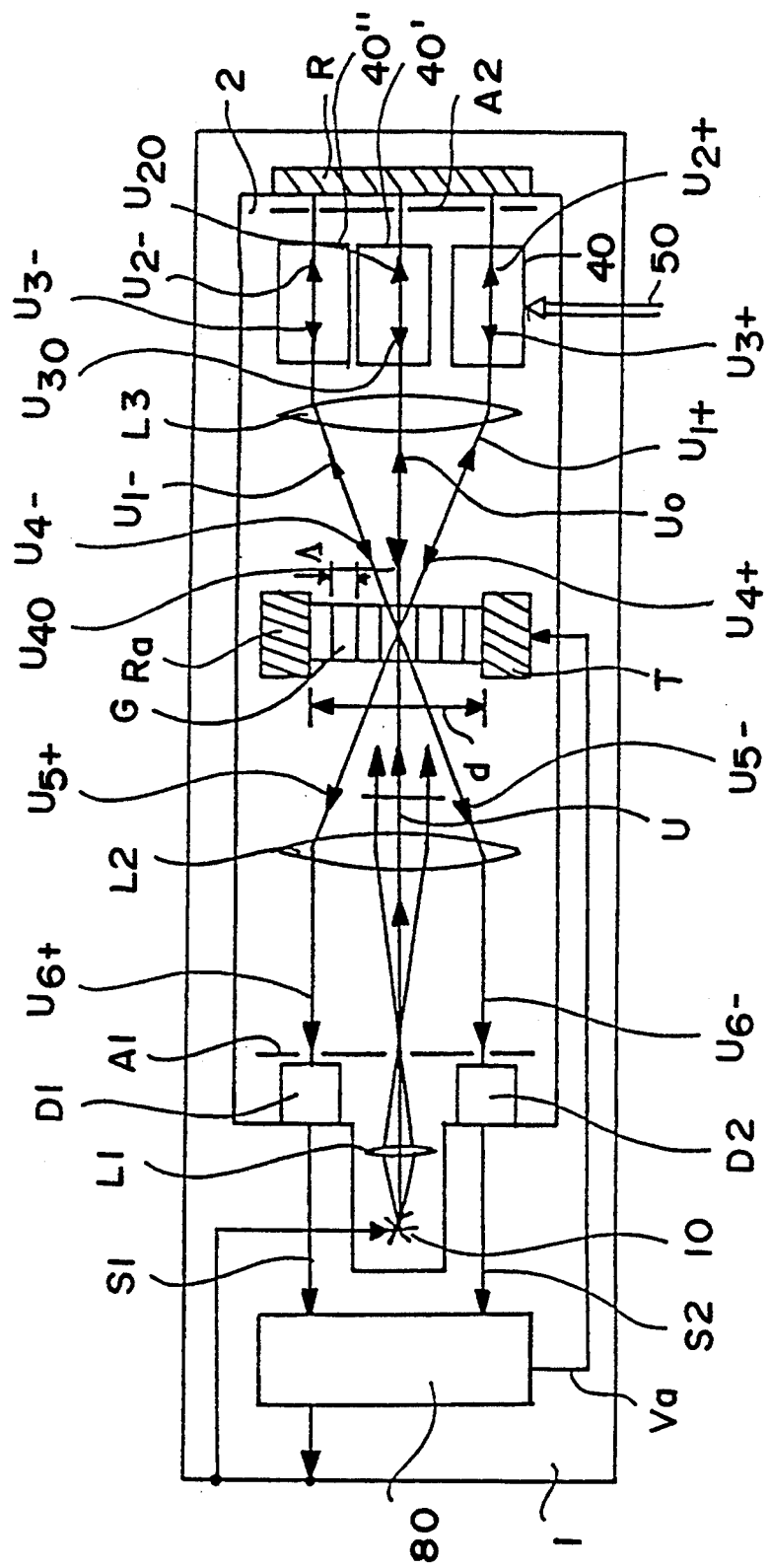
FIG. 20 shows a sensor module which is designed as an integrated optical Fizeau interferometer with a dynamic grating.

FIG. 20 shows an exemplary embodiment involving a modified integrated optical version of a Fizeau interferometer [BORN80, 289–300; BARN87], which serves to determine the phase shift $\phi1+$ effected by the measuring variable 50 in the sensor field 40. The module parameter here is this phase shift $\phi1+$. With the aid of the lenses L1 and L2 and a mask A1 in the planar waveguide 2, a narrow-band light source 10 generates a guided collimated wave u, which is split by a diffraction grating G having a periodicity lambda into the partial wave u1 −, u0 and u1+ corresponding to the diffraction orders of −1, 0 and +1. For the sake of simplicity, only the central beams of the intrinsically expanded beam clusters are otherwise shown. These partial waves are focused by the lens L3 as waves u2+, u20 and u2− onto a reflector R, in front of which, for space filtering, there is a mask A2 of absorbent material, which admits light only at the points of focus. After the reflection at R, the measuring beam u3+ passes through the sensor field 40 a second time. The reference beam u30 and u3− also pass through the reference sensor field 40' and 40" a second time, which increases the sensitivity. The reflected waves u4−, u40 and u4+ now strike the grating G from the back and are diffracted there again. Because of the symmetry of the arrangement, the diffracted waves u5+ and u5− are in principle composed of the components of all the waves u4−, u40 and u4+. However, the grating may be embodied such that only the so-called first diffraction orders actually contain a high power. The wave u5− is thus composed of the undiffracted wave u4− and the first order diffraction wave u40. Analogously, the wave u5+ is composed of the superposition of the null order of u4+ and the first negative order of u40. These two waves are now focused by the lens L2, as waves u6− and u6+, onto the detectors D1 and D2, and the corresponding electrical signals S1 and S2 are processed by the signal processing unit 80. The mask A1 suppresses interfering light (scattered light and light from higher diffraction orders) and simultaneously serves as a space filter for generating the wave u.

From the above it can be seen that the powers $L_+$ and $L_-$ of the waves u6+ and u6− meet the following conditions:

$$L_- \text{ is proportional to } 1+\cos[2(\phi_g+\phi_0+\phi_{1-})] \quad (1)$$

$$L_- \text{ is proportional to } 1+\cos[2(\phi_g+\phi_{1+}+\phi_0)] \quad (2)$$

in which $\phi_g$ is the phase shift that is effected by a single diffraction at the grating. $\phi_0$ is the phase shift which the waves u20 and u30 each undergo upon passing through the reference field 40'. The phase $\phi_{1-}$ and the waves u2− and u3− will be understood by analogy, while $\phi_{1+}$ is the phase shift of the waves u2+ and u3+ in the sensor field 40.

An essential feature of this arrangement is that the diffraction grating G is not rigid but instead is generated dynamically, for instance with the aid of a (surface) acoustic wave or acousto-optically—with the aid of nonlinear integrated optics [BORN80, 596–610; HUNS84, 266–269, 281]. This purpose is served here by a transducer T (ultrasonic transducer), for instance, and an acoustical reflector $R_a$, which in a known way generate a standing acoustic wave and by means of the acoustooptical effect also produce the desired optical phase grating G. The particular feature now is that both the periodicity lambda and the phase position of the grating at the location of the guided waves can be adjusted by means of the frequency $v_a$ of the acoustic wave. In our case, the distance d between the transducer T and the reflector $R_a$ will be selected to be much higher than lambda; as a result, upon a small change in $v_a$, essentially only a shift delta $y(v_a)$ of the grating G occurs, while lambda is practically constant. It is therefore possible to adjust the phase shift $\phi_g$ effected by the grating G in accordance with the following relationship:

$$\phi_g(v_a) = \phi_g(\text{delta } y) = 2\pi \cdot \text{delta } y(v_a)/\text{lambda} \quad (3)$$

and to vary it dynamically as a function of the time t, in accordance with the frequency $v_a(t)$ controlled by the signal processing unit. Diffraction at moving gratings is known and has been described, for instance in [STEV70]. This effect has already been utilized to build a heterodyne Fizeau interferometer [BARN87], although in it a mechanically rotating radial grating was used.

The particular feature of the method of FIG. 20 is on the one hand that the phase shift $\phi_g$ can be adjusted electronically (or optically), and that the phase shift $\phi_0$ and $\phi_{1-}$ in the simplest case do not depend on a variable to be measured. $\phi_0$ and $\phi_{1-}$ are determined by the conditions in the reference fields 40' and 40''. In the simplest case, no actual reference field is necessary. For instance, the influence of the temperature on the refractive index and length of the waveguide 2 can nevertheless be compensated for, because the phase shift $\phi_{1+}$ dependent on the measuring variable affects only the power $L_-$ but not the power $L_{30}$; see equations (1) and (2). The determination of the value of the measuring variable is now done by varying the frequency $v_a$ and hence the phase shift $\phi_g$ (see equation (3)) and measuring the corresponding powers $L_+$ and $L_-$ and comparing them with one another. A special case then exists if precisely identical conditions prevail in the reference field 40' and 40'' and in the sensor field 40. In that case, $\phi_{1-} = \phi_0 = \phi_{1+}$, and with suitable standardization in accordance with equations (1, 2, 3), $$L_-(v_a) = L_+(v_a) = 1 + \cos[2\phi_g(v_a)] \quad (4)$$

in other words, the powers vary in phase. If the measuring variable now effects a variation in the phase shift $\phi_{1+}$, then the functions $L_{31}(v_a)$ and $L_+(v_a)$ vary in a phase-shifted manner, and the value of the measuring variable can be determined from the phase shift of the corresponding detector signals $S_1$ and $S_2$. The method shown here makes it possible to vary the phase shift $\phi_g$ quasi-statically and therefore to make do with low-speed detection and signal processing. If the sensor is high-speed, then the acoustical reflector $R_a$ can be dispensed with and the currently running acoustic wave can be used directly.

Figures 21A, 21B, 21C, 21D, 21E:
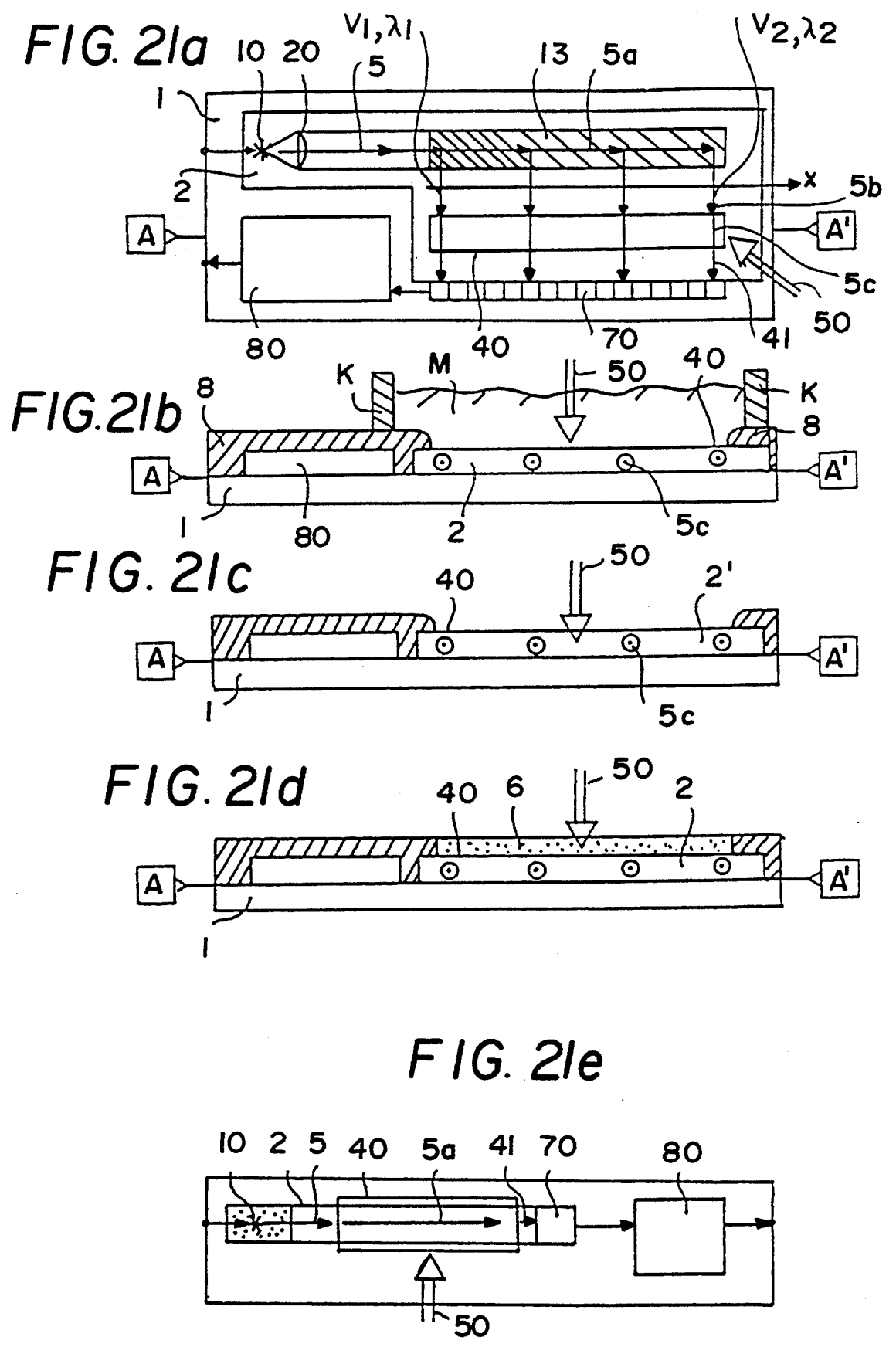

FIG. 21a shows an exemplary embodiment in which the module parameter is the amplitude of the guided wave 41 following the sensor field. As an example, a method for spectral absorption measurement will now be discussed. A rather wide-band light source 10, such as an LED, via a collimator optical element 20, generates a guided wave 5 in the waveguide 2 that then strikes the chirped grating 13. The mode of operation of this grating is analogous to the grating 62 in FIG. 9, but here an entire spectrum of wavelengths lambda 1, . . ., lambda 2 or frequencies V1, . . ., V2 are simultaneously present in the wave 5a. A colored band of diffracted guided waves 5b therefore exists, within which the wavelength varies from lambda 1 to lambda 2, specifically in each case after position x. This band now strikes the sensor field 40, which in the simplest case is a window cut out of the protective layer 8, as shown in the section A-A' of FIG. 21b. The medium M to be analyzed, whose absorption coefficient $\alpha$ represents the variable 50 to be measured, is located in this window, for instance in an optical cell with walls K. The medium may be liquid, solid or gaseous, for example. The interaction with the guided wave 5c is effected in a known manner via the transverse-damped portion of the wave 5c. This type of spectroscopy is known as ATR or total reflection spectroscopy and is described in [HARR67], for example. To achieve stable sensor modules of this type, the waveguide film 2 must be compact and chemically resistant. The RLVIP films described in [KUNZ91] are especially suitable for this purpose. Depending on the absorption spectrum of the medium M, the wave 5c is attenuated variously severely at the various points x, because after all the wavelength varies with x. The local variation in the amplitude or intensity I(x) of the wave 41 striking the detector is therefore a measure of the absorption spectrum in the region of the wavelengths lambda 1 through lambda 2 offered. Absolute measurements may also be performed, based on a calibration measurement with a substance having a known absorption spectrum. Another option is to determine the spectrum of the wave 5b by means of a second, likewise integrated spectrometer without a sensor field, and to take that spectrum into account in the evaluation.

Two further embodiments of the sensor field 40 are shown in FIGS. 21c-d. In FIG. 21c, the sensor field 40 comprises a porous waveguide region 2' which can be entered by substances, such as gases, that can change the complex refractive index of the waveguide film. The result is an absorption of the wave 5c that is wavelength-dependent and hence dependent on the location x, thus enabling a measurement of the absorption spectrum, or in this example a gas analysis. Many further applications and embodiments of the sensor field 40 are possible; the pores may be treated with a chemical substance, for instance, which then reacts selectively with the substances to be analyzed and again varies the complex refractive index. Another option, not shown in the drawings here, is to lend the sensor region of the waveguide thermochromic, electrochromic or similar properties and hence to be able to make a sensor module without windows in the protective layer. With the aid of a thermochromic region, temperatures or temperature gradients above the sensor field can be measured, for instance, because the absorption then depends on the temperature.

FIG. 21d shows a variant in section, in which the sensor field 40 is equipped with a sensor layer 6. Some sensor layers are known, for instance from International Application WO 89/07756 and German Patent 37 23 159, while others have been referred to earlier herein. One valuable option here is to deposit porous layers onto the waveguide film 2 instead of making the waveguide itself porous, because this makes for greater freedom in selecting the materials.

FIG. 21e shows a variant of a sensor module that makes do without a grating 13 and requires only a single detector. The light source 10 is located here in a strip waveguide 2 with a sensor field 40 and a detector 70. This arrangement is suitable for measuring "integral" absorption, because spectral analysis is not done; instead, the total absorption is determined over the spectrum emitted by the light source. If a plurality of such units, but with narrow-band light sources at different wavelengths, are disposed on the same substrate, then it becomes possible to analyze various chemical substances, for instance; in other words, a kind of "artificial nose" could be made, for instance. Other valuable applications are in environmental protection (such as gas analyses and water sampling).

The methods of FIGS. 21a–e can naturally be employed not only for absorption but also for measuring the gain in optically active ("pumped") media. In that case, the wave has more power after the sensor field than when it entered.

Figure 22:
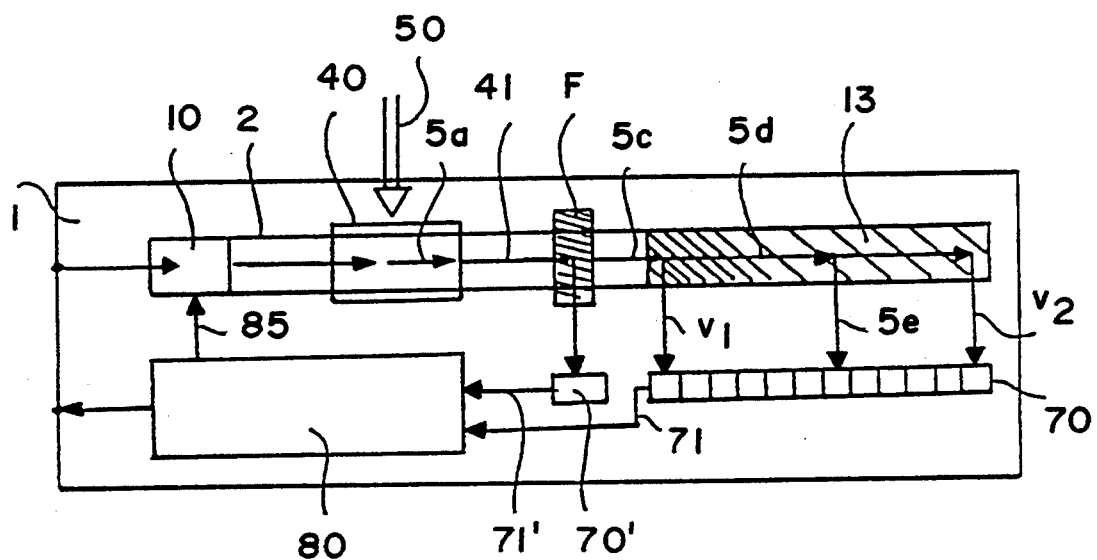
FIG. 22 shows a sensor module with frequency or the frequency spectrum as its module parameter and with an integrated optical spectrometer for determining them.

FIG. 22 shows a variant of a sensor module in which the module parameter is the frequency or the frequency spectrum of the guided wave 41. The arrangement of the light source 10, waveguide 2 and sensor field 40 is selected here in analogy to FIG. 21e. Similarly, the same description as for FIGS. 21b–d applies to the embodiment of the sensor field 40, except that in the method of FIG. 22, the guided wave 5a does not undergo merely attenuation; instead, the incident wave 5 effects a process in the sensor field 40 that varies a frequency spectrum of the guided wave 5a in such a way that frequencies that were not present in the wave 5 also occur. Examples of such processes are fluorescence, nonlinear optical processes, and all types of inelastic light scattering. For certain applications, it may be necessary to filter out the frequencies present in the original wave 5. The plasmon filter F is provided for that purpose, which may for example be embodied as a grating and which removes a certain frequency spectrum from the wave 41 and deflects it to the detector 70'. The transmitted wave 5c then strikes a chirped grating 13, which functions analogously to that of FIG. 21a and breaks down the wave 5d spectrally into partial waves having the frequencies v1, ..., v2. These partial waves, in the form of a beam 5e, strike the detector 70, which is embodied here as an array, whose signal 71 contains the desired spectral information on the measuring variable. To increase the stability and the accuracy, the signal 71' of the detector 70' can be employed in the signal processing unit 80 for regulating the light source 10, by means of the regulating signal 85.

Important fields of application for a sensor module of this kind include measurement of the fluorescence spectrum of substances, measuring and monitoring of nonlinear optical processes, and measuring all types of inelastic light scattering (Raman scattering) in the sensor field.

Figures 23A, 23B:
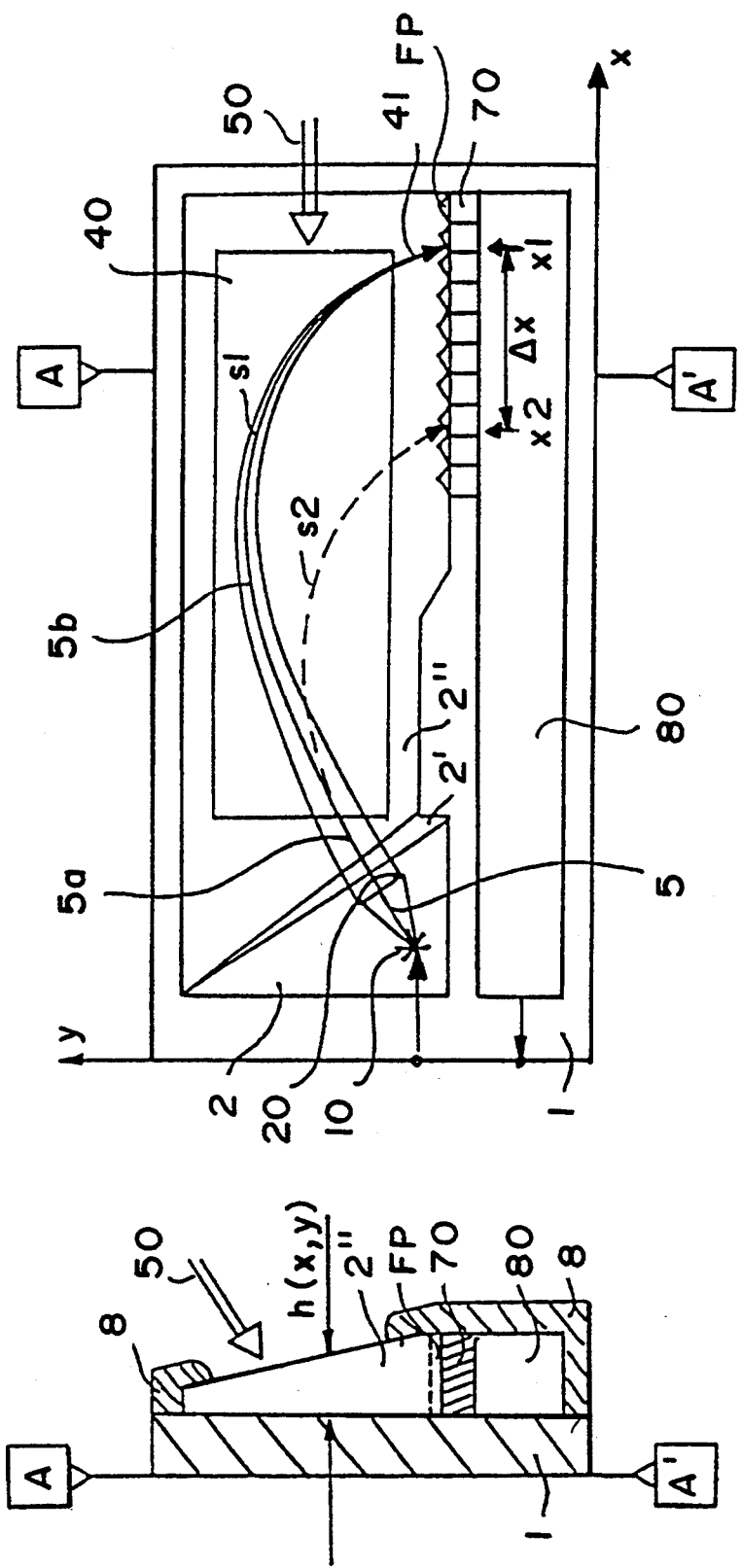

FIG. 23a shows a variant of a sensor module in which the module parameter is the wavelength lambda$_{eff}$ of the guided wave 5b. With the aid of a light source 10 and a collimating optical element 20, a guided wave 5 is generated in a planar waveguide 2. In a transition region 2' of the waveguide, its cross section varies, and then remains constant in a further region 2" but with a suitably selected thickness gradient, as can be seen from the section A-A' of FIG. 23b. Instead of a thickness gradient, a refractive index gradient may also be selected. As has been discussed in conjunction with FIGS. 3 and 4, the effective refractive index N depends on the thickness h(x, y) and hence on the location (x, y) in the waveguide 2". For the sake of simplicity, we will assume here that the thickness varies only in the Y direction, and in such a way that N(y) is less for high values of Y. For the guided wave 5b in the waveguide region 2", the following equations then apply:

lambda$_{eff}$=lambda/N(y) , and $v_p$=c/N(y), in which lambda$_{eff}$ means the effective wavelength, $v_p$ means the phase velocity, lambda means the physical wavelength, and c is either the speed of light in air or a vacuum. Analogously to the so-called Fata Morgana effect, in other words the deflection of a beam of light in the refractive index gradient of air over hot surfaces, the guided wave 5b in the sensor field 40 will now follow a curved path (trajectory) S1, as shown in FIG. 23a. By means of the embodiment of the gradient course h(x, y) and with the aid of the collimating optical element 20, it can be attained that the power of the wave 5b is focused as a wave 41 onto the detector 70 at the point x1. This point depends on the course N(x, y) of the effective refractive index, and hence on the measuring variable 50, because once again we have designed the sensor field 40 in such a way that a variation in the measuring variable at (x, y) effects a variation of N(x, y). Two different values W1 and W2 of the measuring variable accordingly lead to different distributions N1(x, y) and N2(x, y), and hence to different travel distances s1 and s2 or positions x1 and x2, at which the wave 41 meets the detector. The variation in the measuring variable 50 can now be ascertained on the basis of the displacement delta x in the signal processing unit 80.

To attain high sensitivity, it may be suitable to carry the wave 41 to the detector at a vary flat angle. In that case, the efficiency of detection can be improved with the aid of optical elements, such as modified Fresnel prisms FP, in front of the detector.

Figure 24A:
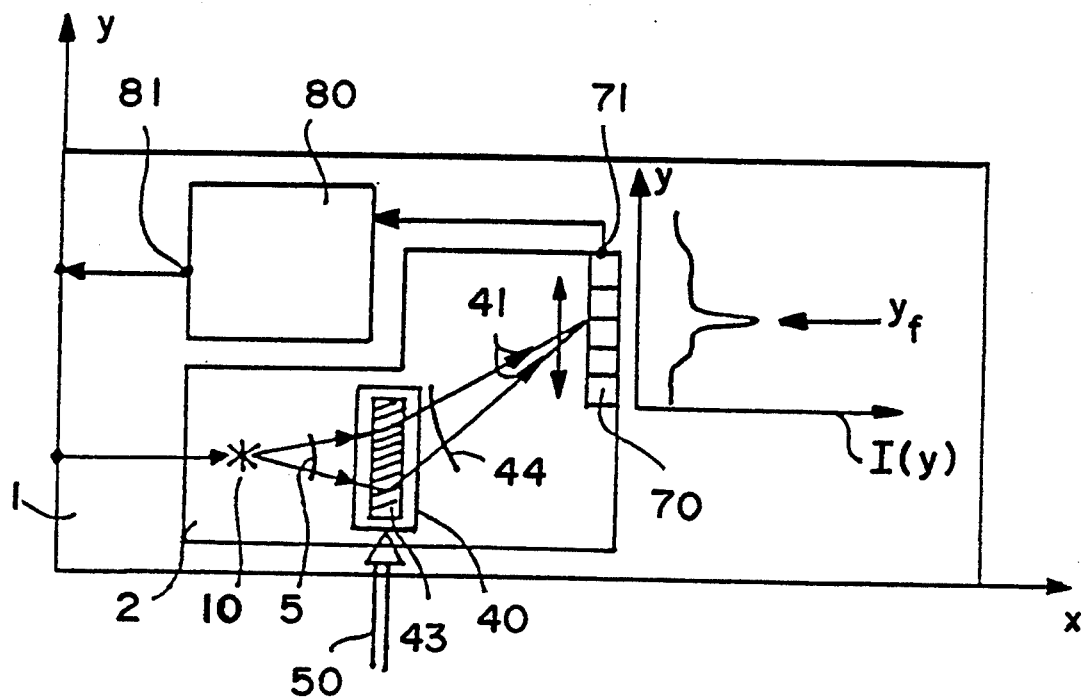
FIG. 24a shows a sensor module with wave front deformation as its module parameter and with a grating lens in the sensor field for determining it.
Figure 24B:
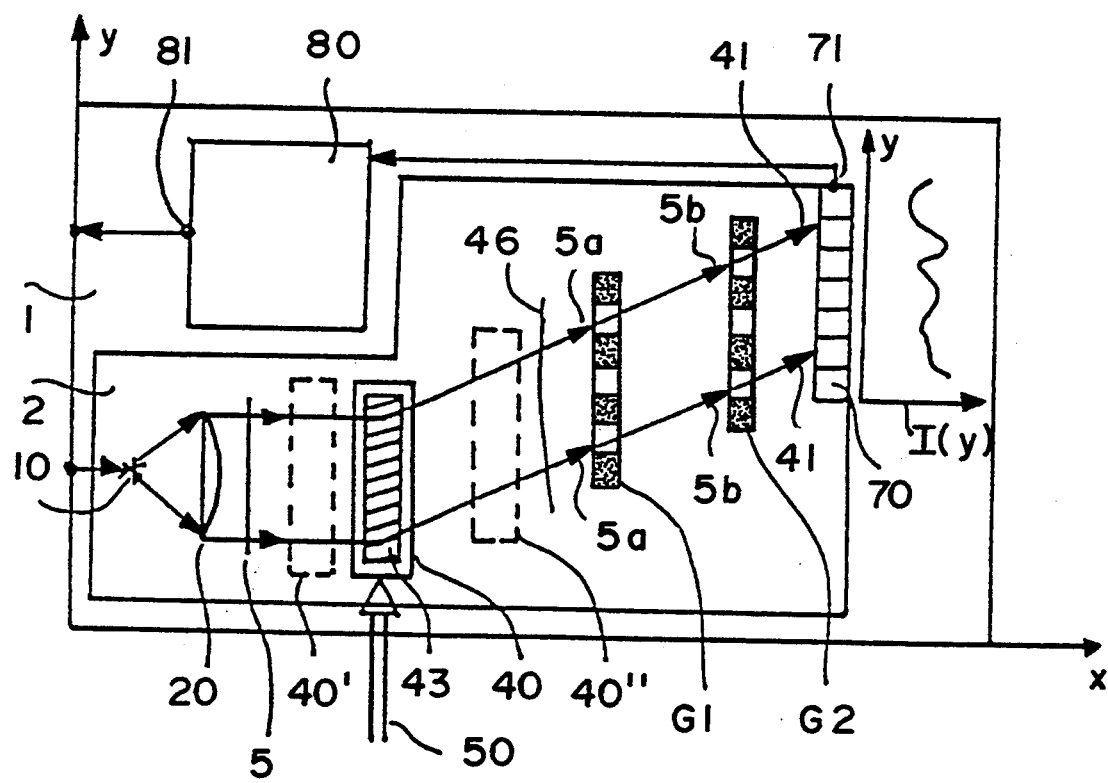
FIG. 24b shows a sensor module with wave front deformation as its module parameter and with a moiré deflectometry arrangement for determining it.

FIGS. 24a–b show two exemplary embodiments, in which the measuring variable 50 in the sensor field 40 causes a deformation D(y) (=module parameter) of the wave front 44 of the guided wave 41 leaving the sensor field 40.

In the arrangement of FIG. 24a, the guided wave 5 generated by the light source 10 is focused with the aid of the grating lens 43 onto the detector 70, analogously to FIG. 12a; the resultant intensity distribution I(y) is converted into a signal 71, and the output signal 81 is generated in the processor 80. The essential difference from the method of FIG. 12a is that the sensor field 40 here is disposed not in the region of the light source 10 but rather in the region of the grating lens 43. A variation in the value W(y) of the measuring variable 50, via the corresponding variation N(y) of the effective refractive index N in the sensor field 40, effects a local modification of the diffractive effect of the grating 43, which results in a variation in the wavefront 44 of the wave 41 and hence a variation in the intensity distribution I(y) on the detector 70. If the light distribution I(y) is not overly complicated, then the variation W(y) can be determined from I(y) by calculation in the processor 80. A particularly simply case exists then if the measuring variable does not depend on y, means in that case its value can be determined from the focus position $y_f$.

FIG. 24b shows an option for how the very sensitive method of moiré deflectometry [GLAT88], known from discrete optics, can be utilized in an integrated optical sensor module to measure even complicated local variations W(y). In a first variant, with the aid of a light source 10 and an optical element 20, a (collimated) wave 5 is generated in the waveguide 2. It strikes the sensor field 40, which is located in the region of a diffraction grating 43. The wave 5a, which corresponds to a selected diffraction order and has the wave front 46, passes through the gratings G1 and G2 and then, as the wave 41, strikes the detector 70. From the intensity distribution I(y) on the detector 70, the deformation D(y) of the wave front 46 effected by the variation W(y) or N(y) in the sensor field 40 can be determined by calculation in the processor 80. The associated formalism can be derived in analogy with the case of discrete optics [GLAT88] and will therefore not be shown here. Finally, the determination of W(y) is effected from D(y), by making use of the relationship D(y)=D(N(W(y))).

Further variants are obtained by disposing the sensor field 40 at a different point 40' and/or 40" before and/or after the region of the grating 43. In the case of a sensor field 40' the grating 43 may be omitted, or work can be done with the zero diffraction order.

What is claimed is:

1. A method for determining the value of one or more variables to be measured by means of an integrated optical sensor module, comprising the steps of:
   providing at least one guided wave in at least one optical waveguide integrated in said sensor module;
   interacting at least one of said guided waves with at least one measuring variable in at least one sensor field arranged integrated in said sensor module to receive said at least one of said guided waves;
   defining the value of at least one module parameter by the action of the measuring variable on the guided wave;
   converting the guided wave into at least one modified guided wave by the action of the measuring variable on the guided wave;
   analyzing said modified guided wave in at least one analyzer integrated in the sensor module to ascertain a value at least one output variable corresponding to the measuring variable; and
   making available said value of said at least one output variable in at least one information field integrated in the sensor module.

2. The method of claim 1, wherein said sensor field, analyzer, and information field are integrated in the sensor module monolithically.

3. The method of claim 1, wherein said value of said at least one module parameter is defined as a resonance of said interaction.

4. The method of claim 1, wherein the step of includes determining the value of the module parameter by means of said interaction, said resonance depending on a condition taken from the group consisting of location, angle, frequency, and wavelength.

5. The method of claim 4, further comprising the step of generating the location-dependent resonance condition by means of a grating in a grating region, and wherein, in the grating region, at least one of grating parameters, thickness of the waveguide, optical properties of the waveguide, and optical properties of the immediate surroundings of the waveguide are location dependent.

6. The method of claim 1, wherein said module parameter is one taken from the group consisting of the phase, amplitude, frequency, effective wavelength, and wave front of the guided wave.

7. The method of claim 1, wherein the properties of at least one of the sensor field and the analyzer are dependent on time in such a manner that a temporal weighting of the measurement effect is performed and a time-dependent resolution is attained.

8. The method of claim 1, wherein the value of the output variable is ascertained as a function of signals of further optical sensor elements.

9. The method of claim 5, wherein the excitation of the guided wave is affected as a function of a controlled variable derived by the analyzer.

10. The method of claim 5, further comprising the step of:
    overcoupling the guided wave into at least one further waveguide;
    interacting said overcoupled guided wave in said further waveguide with the measuring variable; and
    further processing the modified guided wave in one of the following: the further waveguide and the wave guide, after being coupled back into the waveguide.

11. The method of claim 5, further comprising the step of
    further interacting the modified guided wave leaving the sensor field in at least one further sensor field with at least one further variable to be measured;
    analyzing the further modified wave after said further interaction; and
    storing information representing the collective interaction of the measuring variables in the information field.

12. The method of claim 1, wherein said sensor field, analyzer, and information field are integrated in the sensor module as a set of compatible processes.

13. The method of claim 1, wherein the properties of at least one of the sensor field and the analyzer are made dependent on location in such a manner that a spatial weighting of the measurement effect is performed and a location-dependent resolution is attained.

14. The method of claim 1, wherein the properties of at least one of the sensor field and the analyzer are made dependent on both location and time in such a manner that both a spatial and temporal weighting of the measurement effect is performed and both a location-dependent and time-dependent resolution are attained.

15. The method of claim 1, wherein the output variable is ascertained as a function of signals of further non-optical sensor elements.

16. The method of claim 1, wherein the output variable is ascertained as a function of signals of further optical and non-optical sensor elements.

17. An apparatus comprising:
    an integrated optical sensor module, the sensor module including:
        at least one optical waveguide integrated in said sensor module;
        at least one guided wave in said at least one optical waveguide;
        at least one sensor integrated in said sensor module field for ascertaining the interaction of the guided wave with at least one measuring variable;
        at least one analyzer integrated in said sensor module for ascertaining at least one output variable corresponding to the measuring variable; and at least one information field integrated in said sensor module for making the output variable available.

18. The apparatus of claim 17, wherein the sensor module components are on a single substrate, and the components arrangement is a monolithic structure in one or more layers.

19. The apparatus of claim 17, further comprising a light source integral with the sensor module to excite the guided wave.

20. The apparatus of claim 19, wherein the light source is one of a laser diode and a light-emitting diode.

21. The apparatus of claim 17, further comprising an energy source for supplying energy required to operate the sensor module, said energy source being external to the sensor module and in the form of one of a battery, a chemical energy source, and a nuclear energy source.

22. The apparatus of claim 17, further comprising an external light source to excite the guided wave in the form of one of a laser diode and a light-emitting diode optically coupled to said waveguide by an optical fiber.

23. The apparatus of claim 17, wherein said at least one sensor field is a subregion of the waveguide, wherein the optical properties of said subregion are influenced by the measuring variable, said subregion having a property taken from the group consisting of magnetooptical, electrooptical, nonlinear optical, piezooptical, thermooptical, chemooptical, elastooptical, biooptical acoustooptical, optical properties dependent on the type of incident particle radiation, and optical properties dependent on an intensity of incident particle radiation.

24. The apparatus of claim 17, wherein the sensor field contains at least one sensor layer, said sensor layer having a property taken from the group consisting of magnetooptical, electrooptical, nonlinear optical, piezooptical, thermooptical, chemooptical, elastooptical, biooptical, acoustooptical properties, optical properties dependent on the type of incident particle radiation, and optical properties dependent on an intensity of incident particle radiation.

25. The apparatus of claim 17, wherein the value of the output variable is one of an electrical signal, optical signal, acoustical signal, electromagnetic signal, chemical signal, and a mechanical signal.

26. The apparatus of claim 17, wherein the information field includes one of an electrical contact, at least one optical fiber connection, at least one optical display field, at least one acoustical emitter, at least one high-frequency emitter, at least one chemically active boundary junction, at least one mechanical force coupler, and at least one thermal coupler.

27. The apparatus of claim 17, wherein said at least one sensor field includes a uniform Bragg grating, which is disposed in the region of a nonuniform waveguide.

28. The apparatus of claim 17, wherein said at least one sensor field includes a nonuniform Bragg grating which is disposed in the region of a uniform and nonuniform waveguide.

29. The apparatus of claim 17, wherein the analyzer further comprises at least one detector and at least one mask in front of said at least one detector to increase sensitivity.

30. The apparatus of claim 17, further comprising at least one further waveguide, and at least one coupling element disposed to couple said at least one optical waveguide and said at least one further waveguide, the sensor field being disposed in the region of the coupling element.

31. The apparatus of claim 30, wherein the coupling element includes a buffer layer with a property taken from the group consisting of a location-dependent thickness and a location-dependent refractive index.

32. The apparatus of claim 30, wherein said coupling element includes a grating in a grating region, and wherein grating parameters of said grating region are location dependent.

33. The apparatus of claim 17, further comprising at least one plasmon filter between said sensor field and said analyzer for filtering undesirable guided waves.

34. The apparatus of claim 17, wherein the sensor module includes one of the following: further optical and nonoptical sensor elements on the same substrate.

35. The apparatus of claim 27, wherein said analyzer derives a controlled variable for influencing one of a light source, a light forming stage, and an optical filter.

36. The apparatus of claim 27, wherein said at least one guided wave and said at least one sensor field are located in a strip waveguide, and means for processing the guided wave leaving the sensor field are provided in the strip waveguide.

37. The apparatus of claim 36, further comprising a means for generating the guided wave, said generating means being disposed in the strip waveguide.

38. The apparatus of claim 27, further comprising an optical filter for generating the frequency-dependent resonance condition, said optical filter being tuneable by the measuring variable by means of a variation in the effective refractive index in the region of a Bragg grating.

39. The apparatus of claim 38, wherein the filter is one of a resonant-reflective filter and a resonant-transmissive filter.

40. The apparatus of claim 23, further comprising at least one grating for overcoupling of the guided wave form said at least one waveguide into at least one further waveguide.

41. The apparatus of claim 40, wherein the further waveguide is disposed in at least one of the following locations: next to the waveguide in the same layer, in a layer system above the waveguide, on the other side of a substrate upon which said waveguide is located, and further comprising at least one buffer layer located between the waveguide and the further waveguide.

42. The apparatus of claim 17, further comprising an energy source for supplying energy required to operate the sensor module, said energy source being integral to the sensor module and in the form of one of a battery, a chemical energy source, and a nuclear energy source.

43. The apparatus of claim 17, wherein said at least one sensor field is a subregion physically proximate to said waveguide wherein the optical properties of said subregion are influenced by the measuring variable, said subregion having a property taken from the group consisting of magnetooptical, electrooptical, nonlinear optical, piezooptical, thermooptical, chemooptical, elastooptical, biooptical, acoustooptical, optical properties dependent on a type of incident particle radiation, and optical properties dependent on an intensity of incident particle radiation.

44. The apparatus of claim 17, wherein at least one sensor field includes a nonuniform Bragg grating.

45. The apparatus of claim 27, wherein said at least one guided wave and said at least one sensor field are located in a strip waveguide, and means for processing the guided wave leaving the sensor field are provided parallel to the strip waveguide.

* * * * *